United States Patent [19]

Dextraze

[11] Patent Number: 4,769,451
[45] Date of Patent: Sep. 6, 1988

[54] SYNTHESIS OF CARBAPENEMS USING N-SUBSTITUTED AZETIDINONES

[75] Inventor: Pierre Dextraze, Laprairie, Canada

[73] Assignee: Bristol-Myers Company, New York, N.Y.

[21] Appl. No.: 765,767

[22] Filed: Aug. 15, 1985

[51] Int. Cl.$^4$ .............................................. C07D 487/04
[52] U.S. Cl. ..................................... 540/350; 540/351
[58] Field of Search ................................. 540/350, 351

[56] References Cited

U.S. PATENT DOCUMENTS

| 4,208,422 | 6/1980 | Christensen et al. | 540/350 |
| 4,234,596 | 11/1980 | Christensen et al. | 540/350 |
| 4,318,912 | 5/1982 | Christensen et al. | 540/350 |
| 4,383,946 | 5/1983 | Christensen et al. | 540/350 |

OTHER PUBLICATIONS

M. Anatani et al., Tetrahedron Letters, vol. 23, No. 38, pp. 3921–3924, (1982).
T. Kametani, Heterocycles, vol. 17, pp. 463, 495 and 496, (1982).

*Primary Examiner*—Robert Gerstl
*Attorney, Agent, or Firm*—R. E. Carnahan

[57] ABSTRACT

A novel process is disclosed for converting known 3,4-disubstituted azetidinones to carbapenems. The process proceeds through novel N-substituted intermediates and then cyclizes to the 4-position of the azetidinone to form the carbapenem.

11 Claims, No Drawings

SYNTHESIS OF CARBAPENEMS USING N-SUBSTITUTED AZETIDINONES

BACKGROUND OF THE INVENTION

1. Field of the Invention

The present invention is directed to a novel process, which utilizes novel intermediates described herein, for synthesizing carbapenem compounds.

2. Description of the Prior Art

Total syntheses of carbapenems having the generic formula

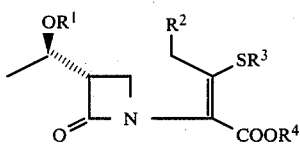

wherein
$R^1$ is hydrogen or a conventional hydroxy-protecting group, and
$R^2$, $R^3$, and $R^4$ are independently selected from the group consisting of hydrogen; substituted and unsubstituted: alkyl, alkenyl, and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and herterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties having 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms;
often start with an optically active azetidinone intermediate such as that of Formula II

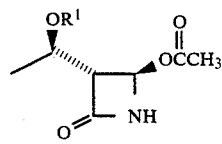

wherein $R^1$ is hydrogen or a conventional hydroxy-protecting group and wherein the absolute configuration at carbons 1', 3 and 4 is R, R and R. Intermediates of Formula II, which are known per se, are key intermediates in the synthesis of carbapenem and penem antibiotics having an (R)-hydroxyethyl substituent at the 6-position of the carbapenem or penem nucleus and the absolute configuration R and S at the 5 and 6-positions, respectively. A wide variety of such compounds, including the natural fermentation product thienamycin, have been reported in the patent and scientific literature as having exceptional antibacterial activity.

Several total synthesis procedures have been reported for preparation of the above-described penem and carbapenem antibiotics, but to date suc procedures have been unsatisfactory from a commercial standpoint due to the large number of steps required and the necessity of separating diastereisomer mixture formed in such procedures.

As previously mentioned, these total synthesis procedures often start with compounds such as Formula II. Then, through a series of reactions directed at the 4-position substituent, an intermediate is synthesized which can, by conventional methods, be cyclized by reaction with the 1-position nitrogen. A synthesis of this type is illustrated in columns 4 and 5 of U.S. Pat. No. 4,383,946 to Christensen et al, and columns 2 and 3 of U.S. Pat. No. 4,318,912 to Christensen et al.

Other approaches to total synthesis, such as that shown in column 2 of U.S. Pat. No. 4,208,422 to Christensen et al, and columns 11 and 12 of U.S. Pat. No. 4,234,596 to Christensen et al, involve cyclizing intermediates substituted on both the 4-position carbon and 1-position nitrogen.

The novel process of this invention, however, proceeds through novel N-substituted azetidinone intermediates and then cyclizes to the 4-position of the azetidinone, thereby forming a carbapenem.

SUMMARY OF THE INVENTION

The present invention is directed to a novel process for synthesizing carbapenems of the generic formula

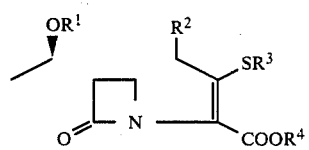

wherein
$R^1$ is hydrogen or a conventional hydroxy-protecting group, and
$R^2$, $R^3$, and $R^4$ are independently selected from the group consisting of hydrogen; substituted and unsubstituted: alkyl, alkenyl, and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties having 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms.

The compounds of Formula I are potent antibacterial agents or intermediates useful in the preparation of such agents.

The process may conveniently be summarized by the following reaction diagram:

DIAGRAM 1

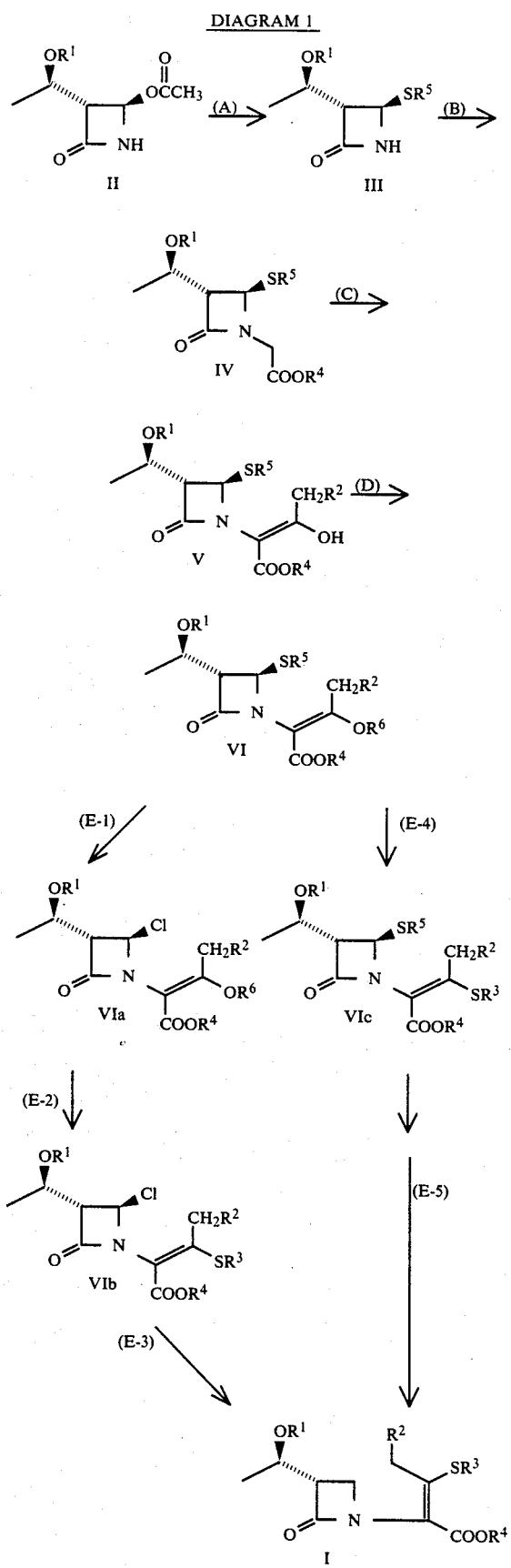

DETAILED DESCRIPTION OF THE INVENTION

Referring now to Diagram 1, the starting material for the carbapenem synthesis is a 3,4-disubstituted azetidinone (Formula II), wherein $R^1$ is hydrogen or a conventional hydroxy-protecting group. Hydroxy-protecting groups, which are known to those skilled in the art, are desirable because they prevent side reactions and provide increased yields in later steps of the reaction sequence. Suitable hydroxy-protecting groups may be, for example, acyl groups such as benzyloxycarbonyl, benzhydryloxycarbonyl, trityloxycarbonyl, p-nitrobenzyloxycarbonyl and 2,2,2-trichlorethoxycarbonyl, aralkyl groups such as benzyl, benzhydryl, trityl or p-nitrobenzyl or triorganosilyl groups such as tri($C_1$–$C_6$)-alkylsilyl (e.g. trimethylsilyl, triethylsilyl, triisopropylsilyl, isopropyldimethylsilyl, t-butyldimethylsilyl, methyldiisopropylsilyl or methyldi-t-butylsilyl), triarylsilyl (e.g. triphenylsilyl, tri-p-xylylsilyl) or triaralkylsilyl (e.g. tribenzylsilyl). Examples of these and other suitable hydroxy-protecting groups and methods for their formation and removal are known in the art, e.g. see *Protective Groups in Organic Synthesis*, T. W. Greene, John Wiley & Sons, New York, 1981, Chapter 2.

The hydroxy-protecting group selected is preferably one that is readily removable at a later stage of the reaction process. Bulkyl triorganosilyl groups such as triisopropylsilyl, t-butyldiphenylsilyl or t-butyldimethylsilyl are advantageously employed because they provide for an essentially stereocontrolled reduction step. Such groups can be readily removed under mild conditions, e.g. by treatment with methanolic HCl or with fluoride ion (e.g. tetra-n-butylammonium fluoride/tetrahydrofuran), which preserve the sensitive β-lactam nucleus.

The conversion of Step (A), wherein a compound of Formula II is converted to the intermediate of Formula III, is carried out under cooling, advantageously between about $-20°$ C. and $10°$ C., and in the presence of an inorganic base. Suitable inorganic bases can include alkali or alkaline earth metal hydroxides, carbonates or bicarbonates (e.g. sodium hydroxide, potassium hydroxide, potassium carbonate, sodium bicarbonate, calcium hydroxide, magnesium hydroxide, etc.), ammonium hydroxide and the like.

In the conversion of compound II to compound III, the 4-position acetoxy is replaced with the residue of a S-nucleophile such as an aliphatic, aromatic, araliphatic, or heterocyclic thiol compound. S-nucleophiles may be employed in a form of a salt such as an alkali metal salt (e.g. sodium salt, potassium salt, etc.), and an alkaline earth metal salt (e.g. magnesium salt, calcium salt, etc.), or the like. Thus, $R^5$ comprises a radical selected from the group consisting of substituted and unsubstituted: alkyl, alkenyl, and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties have 1-6 carbon atoms. A solvent is generally employed such as tetrahydrofuran, diethyl ether, methanol, ethanol, isopropanol, acetic acid, mixtures of ether and alcohol solvents, etc. Compound II can be added dropwise to the S-nucleophile/base/solvent solution which can contain up to a fivefold excess of S-nucleophile. The mixture is advantageously allowed to react for a period of one to four hours under a nitrogen atmosphere before further processing.

In the conversion of Step (B), an acetate group is bonded to the ring nitrogen of the azetidinone. The reaction is carried out under cooling, advantageously below about −50° C., and in the presence of a base and an inert solvent such as tetrahydrofuran. Suitable bases can include organolithium compounds such as lithium bis(trimethylsilyl)amide. Suitable acetate reactants can include, for example, aliphatic, aromatic, araliphatic or haloaliphatic haloacetates, such as methyl bromoacetate, 2-chloroallyl bromoacetate, or phenyl bromoacetate. Up to a threefold excess of acetate reactant can be added dropwise to the solution of compound III in the solvent and base. The reaction can advantageously be carried out under nitrogen for about one to three hours before further treatment.

Alternatively, the conversion of Step (B) can be carried out without cooling by reacting a compound of Formula III with a suitable acetate reactant in the presence of a solvent such as dry tetrahydrofuran, an inorganic base such as potassium hydroxide, and a stereospecific catalyst such as a tetra-n-butylammonium halide. This alternative method can be carried out by adding the base portionwise to a solution comprising compound III, solvent, and up to a threefold excess of acetate reactant. The mixture can be allowed to react for up to 20 hours.

Regardless of the method chosen, $R^4$ is as defined above relative to the final product.

The conversion shown in Step (C) of Diagram 1 is accomplished under cooling, advantageously below −50° C., and in the presence of a solvent, and a base such as an organolithium compound. The conversion can be accomplished by reacting compound IV with an acid chloride of the formula

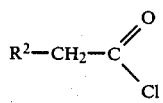

wherein $R^2$ is as defined above relative to the final product. Exemplary of such compounds are acetyl chloride, propionyl chloride, butyroyl chloride, etc.

One advantage of this novel synthesis is evident when $R^2$ is a lower alkyl such as methyl. Upon cyclization, the lower alkyl will substitute the carbapenem in the 1-position. Carbapenems thus substituted have been found to possess advantageous antibiotic properties. When $R^2$ represents hydrogen, the corresponding carbapenem will be unsubstituted in the 1-position.

In the conversion of Step (D) shown in Diagram 1, the hydrogen of the thus formed hydroxy group is replaced with an activating group which will activate the oxygen such that it can be displaced. Suitable activating groups include, for example, methanesulfonyl and p-toluenesulfonyl. Thus, $R^6$ in compound VI is methanesulfonyl or p-toluenesulfonyl. The conversion is advantageously accomplished under cooling and in the presence of a solvent and a tertiary amine catalyst, such as, for example, triethylamine. The reaction can be carried out under a nitrogen atmosphere by adding up to a threefold excess of activating group, which is usually in the chloride salt form, dropwise to a mixture comprising compound V, solvent and catalyst. The mixture can be allowed to react for up to a few hours to insure maximum conversion.

As seen in Diagram 1, the reaction sequence may take one of two different routes between the compounds of Formulas VI and I.

In Step (E-1), the 4-position substituent of the azetidinone is replaced with chlorine to yield a compound of the Formula VIa. The conversion is carried out in a nitrogen atmosphere and under cooling, advantageously less than −50° C., by dissolving compound VI in a solvent such as dichloromethane, and adding an excess of chlorine for up to a few hours to yield compound VIa. The excess chlorine can be in the form of, for example, a solution of chlorine in carbon tetrachloride.

The newly formed intermediate VIa can then be treated, in the same reaction vessel if desired, to yield intermediate VIb, as shown in Step (E-2). To yield compound VIb, compound VIa is reacted with a S-nucleophile in the presence of a tertiary amine catalyst such as diisopropylamine. Suitable S-nucleophiles are described in connection with Step (A). The conversion of Step (E-2) is also carried out under a nitrogen atmosphere, and cooling, advantageously at about below −50° C. Reaction times for Step (E-2) are from about 30 minutes to six hours.

The conversion of Step (E-3) is carried out under a nitrogen atmosphere and cooling, advantageously less than about −50° C., and in the presence of a base, such as, for example, an organolithium compound. Cyclization of compound VIb results from addition of a suitable catalyst such as silver tetrafluoroborate in an inert solvent. The reaction can be carried out by successively treating a solution of compound VIb in a solvent such as dry tetrahydrofuran, with an organolithium base (in solvent), and silver tetrafluoroborate (in solvent). Reaction times can range from about 15 minutes to about two hours.

As shown in Diagram 1, a second route to compound I may be taken by converting a compound of Formula VI to intermediate VIc as shown in Step (E-4). In Step (E-4), the activating group is replaced with the residue of a S-nucleophile. Suitable S-nucleophiles are described above in connection with Step (A). The conversion is advantageously accomplished by reacting a solution of compound VI and a dry solvent, with up to a fourfold excess of the S-nucleophile, in the presence of a suitable catalyst such as, for example, diisopropylethylamine. The conversion of Step (E-4) requires from about two to seven hours and does not require cooling.

The conversion of Step (E-5) can be accomplished by first converting the $SR^5$ group to a better leaving group. For example, the $SR^5$ group can be oxidized to a sulfoxide or converted to a sulfonium group using alkylating agents such as methyl iodide, methyl triflate, trimethyl fluoroborate, etc., or mercury salts such as mercury triflate, etc.

Then, in a manner similar to the conversion of Step (E-3), the sulfonium or sulfoxide is displaced by the nucleophile formed at the $R^2$ position. The nucleophile, which is a carbanion generated by the addition of base, must enter the beta-face of the molecule due to the presence of the large 3-position substituent on the alphaface. In the case where the SR[5] group is activated by a mercury salt, the carbanion can be generated before or after the addition of the mercury salt by a strong base at low temperature.

The following examples illustrate but do not limit the scope of the present invention. All temperatures referred to below are in degrees Celsius, unless otherwise indicated.

Example 1 illustrates the entire synthesis, as shown in Steps (A), (B), (C), (D), (E-1), (E-2) and (E-3), wherein a compound of Formula II is converted to a compound of Formula I.

EXAMPLE 1

Step (A)

Preparation of (3S,4R) 3-(1R-t-butyldimethylsilyloxyethyl)-4-phenylthioazetidinone

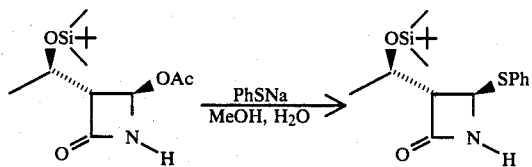

To a cold (5°–10° C.) solution of sodium hydroxide (3.4 g, 0.085 mol) in water (40 mL) kept under a nitrogen atmosphere was added a solution of thiophenol (12.34 g, 0.112 mol) in methanol (80 mL). The cooling bath was removed and the mixture was stirred for 0.5 hour and then treated with a solution of (3R,4R) 4-acetoxy-3-(1R-t-butyldimethylsilyloxyethyl)azetidinone (25.0 g, 0.087 mol) in methanol (200 mL). The reaction mixture was stirred for 2.5 hours. The crystals were filtered and washed with cold methanol, 14.9 g, mp 114°–9° C., 50.7%. The filtrate was concentrated to about half of the initial volume and then diluted with water (80 mL). The precipitate was filtered off and washed with cold methanol, 10.1 g, mp 114°–9° C., 34.4%. The filtrate was extracted with dichloromethane (1×250 mL, 1×80 mL) and the organic extracts were combined, washed with water (2×50 mL) and brine, and dried over magnesium sulfate. The crude material was chromatographed on silica gel with a mixture of 10% of ethyl acetate in dichloromethane as eluting solvent to give after evaporation of the appropriate fractions 2.6 g, mp 117°–9° C., 8.3% for a total yield of 94%. Analytical sample was obtained after one recrystallization from ether-petroleum ether; mp 117°–9° C.; ir (CHCl$_3$) $\nu_{max}$: 3440 (NH), 1768 ($\beta$-lactam), 1588 (phenyl) and 1260 (CH$_3$Si) cm$^{-1}$; [1]Hmr (CDCl$_3$)$\delta$: 0.06 (s, 6H, CH$_3$Si), 0.87 (m, 9H, t-butyl-Si), 1.21 (d, J=6.3 Hz, 3H, CH$_3$CHOSi), 3.03 (m, 1H, H-3), 4.23 (m, 1H, CH$_3$CHOSi), 5.07 (d, J=2.4 Hz, 1H, H-4), 5.95 (brs, 1H, NH), 7.1–7.6 (m, 5H, phenyl); uv (CH$_3$CN) $\lambda_{max}$: 223 ($\epsilon$ 5940) and 251 ($\epsilon$ 4800); [$\alpha$]$_D^{23}$+80° (c 0.61, CHCl$_3$). Anal. calcd. for C$_{17}$H$_{27}$NO$_2$SSi: C 60.49, H 8.06, N 4.15, S 9.50; found: C 60.35, H 8.37, N 4.08, S 9.64.

Step (B)

Preparation of methyl (3S,4R) 3-(1R-t-butyldimethylsilyloxyethyl)-2-oxo-4-phenylthio-1-azetidinylacetate

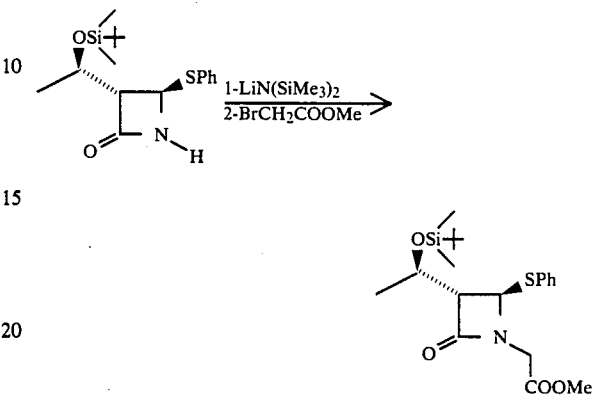

A solution of (3S,4R) 3-(1R-t-butyldimethylsilyloxyethyl)-4-phenylthioazetidinone (10.0 g, 29.6 mmol) in dry tetrahydrofuran (30 mL) was added dropwise to a cold (−70° C.) solution of lithium bis(trimethylsilyl)amide in tetrahydrofuran (31.1 mL, 1.0M, 31.3 mmol) kept under a nitrogen atmosphere. The mixture was stirred at −70° C. for 0.25 hour and treated dropwise with methyl bromoacetate (3.82 mL, 40.3 mmol). The reaction mixture was stirred at −70° C. for 0.75 hour then brought at 23° C. and stirred for another 0.75 hour. The mixture was cooled to −30° C. and diluted with water (60 mL) and dichloromethane (250 mL). The organic phase was separated, washed with brine-water mixture (1:1, 50 mL) and brine (3×50 mL), and dried (MgSO$_4$). Evaporation of the solvents gave the crude title compound (14 g) which was purified by chromatography (silica gel 350 g) with a mixture of 5% ethyl acetate in dichloromethane as eluting solvent. Evaporation of the appropriate fractions gave 11.8 g, 97.2% of a pale yellow syrup; ir (neat) $\nu_{max}$: 1775 (C═O of the $\beta$-lactam), 1755 (C═O of the methyl ester), 1589 (phenyl) and 1260 (CH$_3$Si) cm$^{-1}$; [1]Hmr (CDCl$_3$) $\delta$: 0.05 and 0.07 (2s, 6H, CH$_3$Si), 0.87 (m, 9H, t-butyl-Si), 1.23 (d, J=6.3 Hz, 3H, CH$_3$CHOSi), 3.0 (m, 1H, H-3), 3.66 (s, 3H, CH$_3$O), 4.0 (center of ABq, J$_{ab}$=18.0 Hz, NCH$_2$COO), 4.22 (m, CH$_3$CHOSi), 5.24 (d, J=2.3 Hz, 1H, H-4) and 7.1–7.6 (m, 5H, phenyl); uv (CH$_3$CN) $\lambda_{max}$: 224 ($\epsilon$ 6710) and 251 ($\epsilon$ 4185); [$\alpha$]$_D^{23}$+17.7° (c 1.7, CHCl$_3$). Anal. calcd. for C$_{20}$H$_{31}$NO$_4$SSi: C 58.64, H 7.63, N 3.42, S 7.83; found: C 58.11, H 7.65, N 3.40, S 7.92.

Step (C)

Preparation of methyl 2-[(3S,4R) 3-(1R-t-butyldimethylsilyloxyethyl)-2oxo-4-phenylthio-1-azetidinyl]-3-hydroxycrotonate

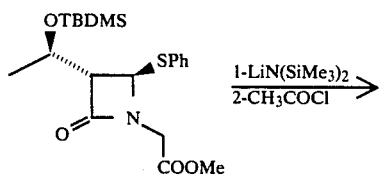

-continued

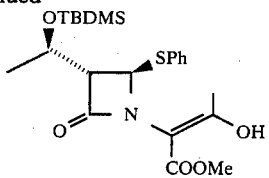

To a cold (−70° C.) solution of lithium bis(trimethylsilyl)amide in tetrahydrofuran (53.4 mL, 1.0M, 53.4 mmol) kept under a nitrogen atmosphere was added a solution of methyl (3S,4R) 3-(1R-t-butyldimethylsilyloxyethyl)-2-oxo-4-phenylthio-1-azetidinylacetate (9.94 g, 24.3 mmol) in dry tetrahydrofuran (60 mL). The mixture was stirred at −70° C. for 0.25 hour and treated with acetyl chloride (1.7 mL, 23.9 mmol). The mixture was stirred for 35 minutes at −70° C. and diluted with water (145 mL) containing acetic acid (1.08 mL, 18.9 mmol) and dichloromethane (800 mL). The organic phase was separated, washed with brine (5×100 mL), dried (MgSO$_4$) and passed through a silica gel pad (100 g, 9.0×3.5 cm); the products were eluted with a mixture of 30% of ethyl acetate in dichloromethane (700 mL). The two solutions were combined and concentrated to give 11.0 g of crude material which was purified by a column chromatography (silica gel, eluent: 10% ethyl acetate in toluene). Evaporation of the appropriate fractions gave 6.9 g, (63%) of the title compound as a pale yellow syrup; ir (neat) $\nu$max: 1762 (C=O of $\beta$-lactam), 1655 (C=O of ester), 1615 (C=C of enol) and 1250 (CH$_3$Si) cm$^{-1}$; $^1$Hmr (CDCl$_3$) $\delta$: 0.04 and 0.08 (2s, 6H, CH$_3$Si), 0.86 (m, 9H, t-butyl-Si), 1.29 (d, J=6.3 Hz, 3H, CH$_3$CHOSi), 2.09 (s, 3H, CH$_3$C(OH)=C), 3.14 (dd, J=4.3 Hz, J=2.8 Hz, 1H, H-3), 3.55 (s, 3H, CH$_3$O), 4.2 (m, 1H, CH$_3$CHOSi), 5.35 (d, J=2.8 Hz, H-4), 7.25 (m, 5H, phenyl) and 12.25 (s, 1H, OH). Anal. Calcd. for C$_{22}$H$_{33}$NO$_5$SSi: C 58.51, H 7.36, N 3.10, S 7.10; found: C 58.74, H 7.37, N 2.97, S 7.04.

Step (D)

Preparation of methyl 2-[(3S,4R) 3-(1R-t-butyldimethylsilyloxyethyl)-2-oxo-4-phenylthio-1-azetidinyl]-3-methylsulfonyloxycrotonate

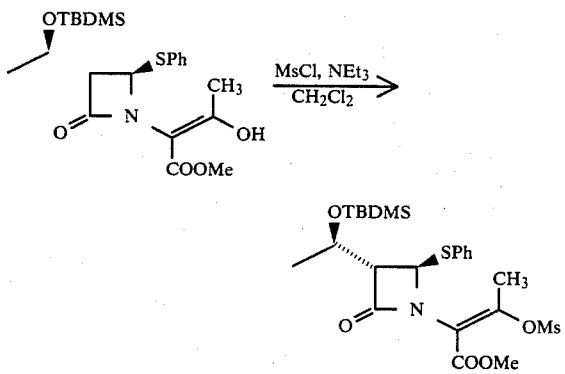

To a cold (0° C.) mixture of methyl 2-[(3S,4R) 3-(1R-t-butyldimethylsilyloxyethyl)-2-oxo-4-phenylthio-1-azetidinyl]-3-hydroxycrotonate (0.837 g 1.85 mmol) and triethylamine (0.32 mL, 2.29 mmol) in dichloromethane (10 mL) kept under a nitrogen atmosphere was added dropwise methanesulfonyl chloride (0.16 mL, 2.07 mmol). The reaction mixture was stirred at 0° C. for 1 hour and diluted with dichloromethane (25 mL). The organic solution was washed with cold water (2×10 mL) and brine, dried (Na$_2$SO$_4$) and concentrated. The crude material was purified by column chromatography (silica gel) with 10% ethyl acetate in toluene as eluent. Evaporation of the appropriate fractions gave the title compound 0.817 g, 83%, as a E/Z mixture. A small amount of E/Z mixture was rechromatographed to give the two pure isomers: isomer E; $^1$Hmr (CDCl$_3$) $\delta$: 0.05 and 0.09 (2s, 6H, CH$_3$Si), 0.87 (m, 9H, t-butyl-Si), 1.32 (d, J=6.3 Hz, 3H, CH$_3$CHOSi), 2.21 (s, 3H, CH$_3$C(OMs)=C), 3.23 (s, CH$_3$SO$_3$), 3.54 (s, 3H, CH$_3$O), 4.25 (m, 1H, CH$_3$CHOSi), 5.48 (d, J=2.9 Hz, H-4), 7.1-7.6 (m, 5H, phenyl); uv (CH$_3$CN) $\lambda_{max}$: 224 ($\epsilon$ 10335), 251 ($\epsilon$ 7544); [$\alpha$]$_D^{23}$+127° (c 0.7, CHCl$_3$); isomer Z; ir (neat) $\nu_{max}$: 1770 (C=O of $\beta$-lactam), 1728 (C=O of ester), 1635 (C=C of enolmesylate), 1375 and 1265 (sulfonate) cm$^{-1}$; $^1$Hmr (CDCl$_3$) $\delta$: 0.05 and 0.08 (2s, 6H, CH$_3$Si), 0.87 (m, 9H, t-butyl-Si), 1.29 (d, J=6.3 Hz, 3H, CH$_3$CHOSi), 2.62 (s, 3H, CH$_3$C(OMs)=C, 3.18 (s, CH$_3$SO$_3$), 3.51 (s, 3H, CH$_3$O), 4.20 (m, 1H, CH$_3$CHOSi), 5.50 (d, J=2.8 Hz, 1H, H-4), 7.1-7.6 (m, 5H, phenyl); uv (CH$_3$CN) $\lambda_{max}$: 224 ($\epsilon$10030), 250 ($\epsilon$7519); [$\alpha$]$_D^{23}$+88.6° (c 0.75, CHCl$_3$). Anal. calcd. for C$_{23}$H$_{35}$NO$_7$S$_2$Si: C 52.14, H 6.65, N 2.64, S 12.10; found: C 52.19, H 6.50, N 2.36, S 12.14.

Steps (E-1) and (E-2)

Preparation of methyl 2-[(3S, 4R) 3-(1R-t-butyldimethylsilyloxyethyl)-4-chloro-2-oxo-1-azetidinyl]-3-phenylthiocrotonate

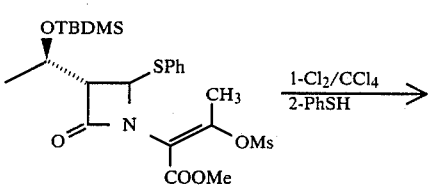

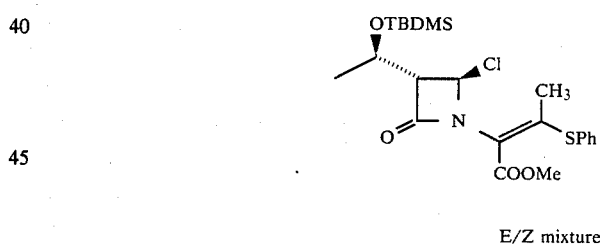

E/Z mixture

To a cold (−70° C.) solution of an E/Z mixture of methyl 2-[(3S,4R) 3-(1R-t-butyldimethylsilyloxyethyl)-2-oxo-3-phenylthio-1-azetidinyl]-3-methylsulfonyloxycrotonate (0.982 g, 1.85 mmol) in dichloromethane (45 mL) kept under a nitrogen atmosphere was added a solution of chlorine in carbon tetrachloride (1.55 mL, 1.22M, 1.89 mmol). The mixture was stirred at −70° C. for 5 minutes and the excess of chlorine was pumpped at −70° C. for 1.0 hour. The resulting mixture was treated successively with diisopropylethylamine (0.71 mL, 4.08 mmol) and thiophenol (0.40 mL, 3.89 mmol), diluted with acetonitrile (9 mL) and warmed up to 0° C. The mixture was stirred at 0° C. for 1 hour, warmed up to 23° C. and concentrated to 10 mL. The stirring was continued for 0.5 hour and the mixture was diluted with ethylacetate (90 mL). The organic solution was washed with water (2×15 mL) and brine, dried (MgSO$_4$) and concentrated to dryness. The crude material was purified by chromatography (silica gel) with a mixture of 20% ether in petroleum ether as eluting solvent. Evaporation of the appropriate fractions gave the title compound, 0.703 g, 81% as E/Z mixture; ir (neat) $v_{max}$: 1772 (C=O of β-lactam) and 1710 (C=O of ester)cm$^{-1}$; $^1$Hmr (CDCl$_3$) δ: 0.07, 0.10 (2s, 6H, CH$_3$Si), 0.89 (s, 9H, t-butyl-Si), 1.31 and 1.33 (2d, J=6.3 Hz, J=6.2 Hz, 3H, CH$_3$CHOSi), 1.90 and 2.23 (2s, CH$_3$C(SPh)=C), 3.39 (dd, J=5.2 Hz, J=1.3 Hz, H-3), 3.52 (dd, J=5.1 Hz, J=1.6 Hz, H-3), 3.77 and 3.83 (2s, 3H, CH$_3$O), 4.2 (m, 1H, CH$_3$CHOSi), 5.92 and 6.07 (2d, J=1.3 Hz, J=1.6 Hz, H-4), 7.2–7.6 (m, 5H, phenyl). Anal. calcd for C$_{22}$H$_{32}$ClNO$_4$SSi: C 56.21, H 6.86, N 2.98, S 6.82, Cl 7.54; found: C 56.49, H 6.77, N 2.82, S 7.04, Cl 7.56.

Step (E-3)

Preparation of (5R,6S) methyl 6-(1R-t-butyldimethylsilyloxyethyl)-7-oxo-3-phenylthio-1-azabicyclo[3.2.0]-hept-2-ene-2-carboxylate

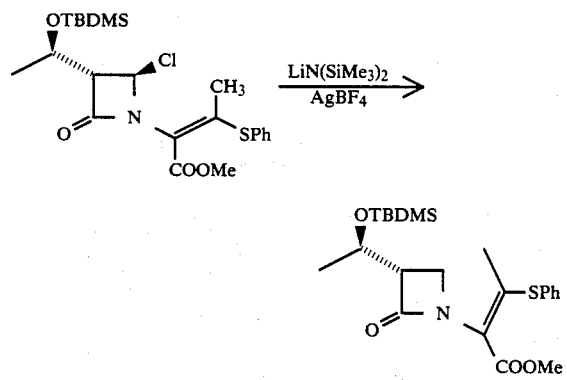

A cold (−78° C.) solution of E/Z mixture of methyl 2-[(3S,4R) 3-(1R-t-butyldimethylsilyloxyethyl)-4-chloro-2-oxo-1-azetidinyl]-3-phenyl-thiocrotonate (0.057 g, 0.121 mmol) in dry tetrahydrofuran (3 mL) kept under a nitrogen atmosphere was treated with a solution of lithium bis(trimethylsilyl)amide in dry tetrahydrofuran (0.130 mL, 1M, 0.13 mmol). The mixture was warmed up to −65° C., stirred for 0.5 hour and treated with a solution of silver tetrafluoroborate in dry tetrahydrofuran (0.57 mL, 0.423M, 0.24 mmol). The mixture was stirred for 10 minutes, acidified with 3 drops of glacial acetic acid and, diluted with brine and ethyl acetate (20 mL). The two phases were separated and the organic phase was washed with water, saturated NaHCO$_3$ solution (4 drops), water and brine, dried (MgSO$_4$) and concentrated to dryness, 0.046 g. The crude material was purified by preparative tlc (50% ether in petroleum ether) to give the title compound, 9 mg, 17%; ir (neat) $v_{max}$: 1782 (C=O of β-lactam), 1730 and 1709 cm$^{-1}$; $^1$Hmr (CDCl$_3$) δ: 0.04 (m, CH$_3$Si), 0.84 (m, t-butyl-Si), 1.17 (d, J=6.1 Hz, CH$_3$CHOSi), 2.61 (m, H-4), 3.00 (dd, J=6.1 Hz, J=2.6 Hz, H-6), 3.88 (s, CH$_3$O), 3.7–4.3 (m, CH$_3$CHOSi, H-5), 7.1–8.2 (m, phenyl); uv (CH$_3$CN) λ$_{max}$: 315 (ε10093); [α]$_D^{23}$+25.3° (c 0.25 CHCl$_3$); Anal. calcd. for C$_{22}$H$_{31}$NO$_4$SSi: C 60.94, H 7.21, N 3.23, S 7.39; found: C 60.45, H 7.13, N 3.13, S 7.38 and the Z isomer of the starting material, 12 mg, 21%; $^1$Hmr (acetone, d-6) δ: 0.11 and 0.13 (2s, CH$_3$Si), 0.90 (m, t-butyl-Si), 1.32 (d, J=6.3 Hz, CH$_3$CHOSi), 1.90 (s, CH$_3$C(SPh)=C), 3.53 (dd, J=1.5 Hz, J=5.3 Hz, H-3), 3.82 (s, CH$_3$O), 4.2 (m, CH$_3$CHOSi), 6.05 (d, J=1.5 Hz, H-4), 7.2–7.7 (m, phenyl).

Example 2 illustrates the conversion of Step (A).

EXAMPLE 2

Preparation of (3S,4R) 3-(1R-t-butyldimethylsilyloxyethyl)-4-methylthioazetidinone

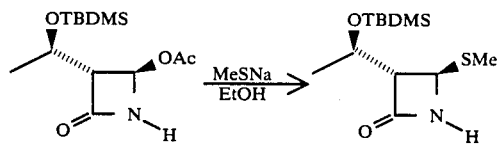

To a cold (−10° C.) solution of potassium hydroxide (1.12 g, 0.02 mol) in ethanol-water mixture (1:3, 40 mL) was added all at once methanethiol (1.4 mL). The mixture was stirred at 0° C. for 1 hour and added dropwise (2.5 hours) to a cold (0° C.) solution of (3R,4R) 4-acetoxy-3-(1R-t-butyldimethylsilyloxyethyl)azetidinone (5.74 g, 0.02 mol) in ethanol (40 mL) at such a rate that the pH of the resulting mixture was kept between 8.7–8.9. After the addition was completed, the reaction mixture was stirred for 0.5 hour at 0° C. and diluted with water (20 mL) and dichloromethane (60 mL). The two phases were separated and the aqueous phase was extracted with dichloromethane (2×40 mL). The organic extracts were combined, washed with water (2×20 mL), dried (MgSO$_4$) and concentrated to a white solid; 5.34 g, mp 75°–82° C., 97%; ir (KBr) $v_{max}$: 3060 (NH), 1755 and 1710 (C=O), 1250 (CH$_3$Si) cm$^{-1}$; $^1$Hmr (CDCl$_3$) δ: 0.08 (m, CH$_3$Si), 0.88 (m, t-butyl-Si), 1.24 (d, J=6.4 Hz, CH$_3$CHOSi), 2.15 (s, CH$_3$S), 3.14 (m, H-3), 4.3 (m, CH$_3$CHOSi), 4.81 (d, J=2.2 Hz, H-4), 5.83 (bs, NH); [α]$_D^{23}$+26.2° (c 0.73, CHCl$_3$). Anal. calcd. for C$_{14}$H$_{25}$NO$_2$SSi: C 52.32, H 9.15, N 5.08, S 11.64; found: C 52.24, H 9.08, N 4.91, S 10.95.

Example 3 illustrates a method for preparing 2-chloroallyl bromoacetate, which is used in Examples 4 and 5.

EXAMPLE 3

Preparation of 2-chloroallyl bromoacetate

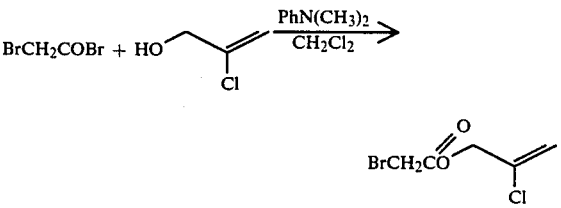

To a cold (0° C.) solution of bromoacetyl bromide (51.5 g, 25.5 mmol) in dichloromethane (80 mL) kept under nitrogen atmosphere was added 2-chloroallyl alcohol (26.0 g, 28.1 mmol) over 5 minutes period and N,N-dimethylaniline (30.9 g, 25.5 mmol) at such a rate that the temperature was kept below 5° C. (30 minutes). When the addition was completed, the cooling bath was removed and, the mixture was stirred for 2 hours at 23° C. and washed with water (25 mL), 0.1N HCl (2×25 mL) and water (25 mL). The organic solution was dried (Na$_2$SO$_4$) and concentrated to a crude material from which the title compound was distilled; 44.8 g, 82%, bp 74°–6° C./1.25 torr; ir (neat) $v_{max}$: 1745 (C=O), 1635

(C=C) cm$^{-1}$; $^1$Hmr (CDCl$_3$) δ: 3.93 (s, BrCH$_2$), 4.73 (s, COOCH$_2$C(Cl)=C$_2$), 5.48 (m, COOCH$_2$C(Cl)=CH$_2$). Anal. calcd. for C$_5$H$_6$O$_2$BrCl: C 28.13, H 2.83, Cl 16.61; found: C 28.49, H 2.92, Cl 16.78

Examples 4–6 each illustrate the conversion of Step (B).

EXAMPLE 4

Preparation of 2-chloroallyl 2-[(3S,4R)3-(1R-t-butyldimethylsilyloxyethyl)-2-oxo-4-phenylthio-1-azetidinyl

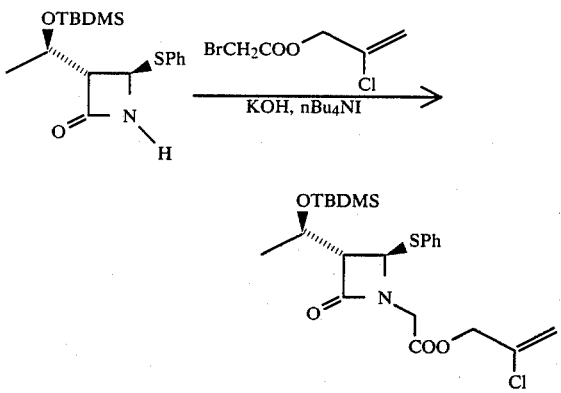

To a solution of (3S,4R) 3-(1R-t-butyldimethylsilyloxyethyl)-4-phenylthioazetidinone (0.40 g, 1.19 mmol), 2-chloroallyl bromoacetate (0.329 g, 1.54 mmol) and tetra-n-butylammonium iodide (0.044 g, 0.12 mmol) in dry tetrahydrofuran (4 mL) was added portionwise at 0.5 hour interval potassium hydroxide (4×0.22 mg, 1.57 mmol). The mixture was stirred at 23° C. for 16 hours and diluted with ethyl acetate (32 mL). The organic solution was washed with brine, dried (MgSO$_4$) and concentrated to dryness. The crude material was purified by preparative tlc (silica gel, 10% ethyl acetate in toluene) to give the title compound as a syrup; 0.31 g, 55.9%; ir (neat) ν$_{max}$: 1770 (C=O's), 1250 (CH$_3$Si) cm$^{-1}$; $^1$Hmr (CDCl$_3$) δ:0.07 (m, CH$_3$Si), 0.88 (m, t-butyl-Si), 1.24 (d, J=6.3 Hz, CH$_3$CHOSi), 3.04 (dd, J=2.3 Hz, J=5.1 Hz, H-3), 3.08 (center of ABq, J$_{a,b}$=18.1 Hz, NCH$_2$COO), 4.65 (m, COOCH$_2$C(Cl)=CH$_2$), 5.27 (d, J=2.3 Hz, H-4), 5.43 (m, COOCH$_2$C(Cl)=CH$_2$), 7.1–7.6 (m, phenyl); uv (CH$_3$CN) λ$_{max}$: 218 (ε9402), 252 (ε3970), [α]$_D^{25}$ −10.9° (c, 1.05, CHCl$_3$); Anal. calcd. for C$_{22}$H$_{32}$NO$_4$SSiCl: C 56.20, H 6.86, N 2.98, S 6.82, Cl 7.54; found: C 56.19, H 7.10, N 3.01, S 6.70, Cl 7.62 and the starting material 0.066 g, 16%.

EXAMPLE 5

Preparation of 2-chloroallyl 2-[(3S,4R)3-(1R-t-butyldimethylsilyloxyethyl)-2-oxo-4-phenylthio-1-azetidinyl

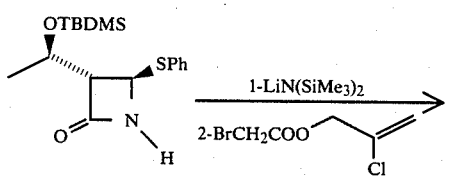

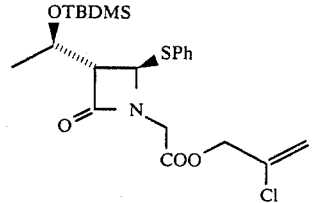

A solution of (3S,4R) 3-(1R-t-butyldimethylsilyloxyethyl)-4-phenyl-thioazetidinone (0.73 g, 2.16 mmol) in dry tetrahydrofuran (3 mL) was added dropwise to a cold (−70° C.) solution of lithium bis(trimethylsilyl)amide in tetrahydrofuran (2.27 mL, 1M, 2.27 mmol) kept under a nitrogen atmosphere. The mixture was stirred at −70° C. for 0.25 hour and treated with 2-chloroallyl bromoacetate (0.645 g, 3.02 mmol). The mixture was stirred at −70° C. for 0.75 hour, warmed up to 23° and stirred for another 0.75 hour before being cooled down to −30° C. and diluted with a mixture of water (4 mL) and dichloromethane (18 mL). The organic phase was separated, washed with water (5×5 mL) and brine, dried (MgSO$_4$) and concentrated to dryness. The crude material was purified by preparative tlc to give 0.35 g, 34.5% of a yellow syrup. The analytical data were identical to those reported in Example 4.

EXAMPLE 6

Preparation of allyl 2-[(3S,4R) 3-(1R-t-butyldimethylsilyloxyethyl)-4-methylthio-2-oxo-1-azetidinyl]acetate

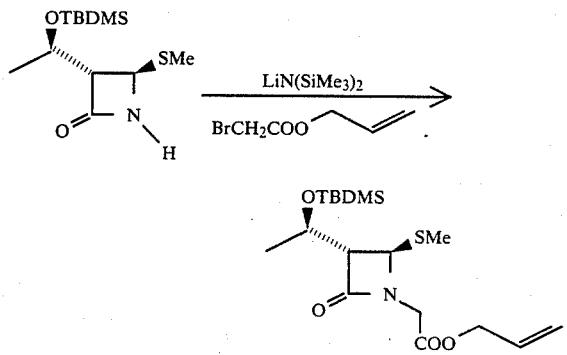

To a cold (−78° C.) solution of 1,1,1,3,3,3-hexamethyldisilazane (3.86 mL, 18.3 mmol) in dry tetrahydrofuran (17 mL) kept under a nitrogen atmosphere was added dropwise a solution of n-butyllithium in tetrahydrofuran (11.5 mL, 155M, 17.8 mmol). The mixture was stirred for 20 minutes and a solution (3S,4R) 3-(1R-t-butyldimethylsilyloxyethyl)-4-methylthioazetidinone (4.7 g, 17.1 mmol) in dry tetrahydrofuran (8 mL) was added. The resulting mixture was stirred at −78° C. for 15 minutes, treated dropwise with allyl bromoacetate (4.26 g, 23.8 mmol), stirred at −78° C. for 1 hour, then at 23° C. for 1 hour and diluted with waterdichloromethane mixture (1:4, 125 mL). The two layers were separated and the aqueous layer was extracted with dichloromethane (50 mL). The organic extracts were combined, washed with brine (5×30 mL), dried (MgSO$_4$) and concentrated. The crude material was purified by chromatography (silica gel: 180 g) using a mixture of 0–5% ethyl acetate in dichloromethane as eluting solvent. Evaporation of the appropriate fractions gave a pale yellow syrup; 3.16 g, 49%; ir (neat) $v_{max}$: 1765 (C=O of β-lactam), 1745 (C=O of ester), 1255 (CH$_3$Si) cm$^{-1}$; $^1$Hmr (CDCl$_3$) δ: 0.06 and 0.08 (2s, CH$_3$Si), 0.87 (m, t-butyl-Si), 1.26 (d, J=6.3 Hz, $\underline{CH_3}$CHOSi), 2.08 (s, CH$_3$S), 3.17 (dd, J=2.2 Hz, J=4.9 Hz, H-3), 3.97 (center of ABq, J$_{ab}$=17.8 Hz, NCH$_2$COO), 4.2 (m, CH$_3$$\underline{CH}$OSi), 4.68 (m, $\underline{CH_2}$CH=CH$_2$), 4.89 (d, J=2.2 Hz, H-4), 5.1-5.5 (m, CH$_2$CH=$\underline{CH_2}$), 5.6-6.2 (m, CH$_2$—CH=CH$_2$); [α]$_D^{23}$+154° (c 0.55, CHCl$_3$). Anal. calcd. for C$_{17}$H$_{31}$NO$_4$SSi: C 54.66, H 8.36, N 3.75; found: C, 54.66, H 8.36, N 3.59.

Examples 7-9 illustrate the conversion of Step (C).

EXAMPLE 7

Preparation of methyl 2-[(3S,4R) 3-(1R-t-butyldimethylsilyloxyethyl)-2-oxo-4-phenylthio-1-azetidinyl]-3-ethyl-3-hydroxyacrylate

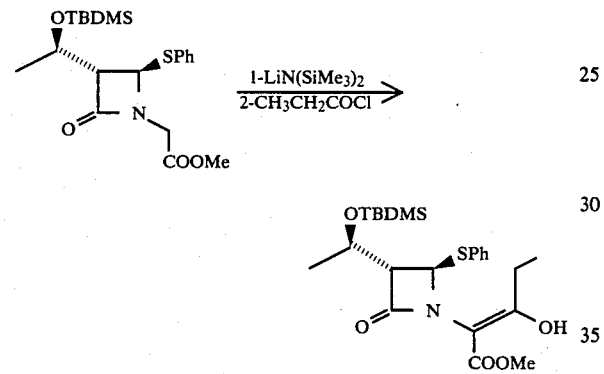

To a cold (−70° C.) solution of lithium bis(trimethylsilyl)amide in tetrahydrofuran (3.77 mL, 1.0M, 3.77 mmol) kept under a nitrogen atmosphere was added a solution of methyl 2-[(3S,4R) 3-(1R-t-butyldimethylsilyloxyethyl)-2-oxo-4-phenylthio-1-azetidinyl]acetate (0.702 g, 1.71 mmol) in dry tetrahydrofuran (4.5 mL). The mixture was stirred at −70° C. for 0.25 hour and treated with propionyl chloride (0.156 mL, 1.8 mmol). The mixture was stirred for 35 minutes at −70° C. and, diluted with water (10 mL) and dichloromethane (60 ml). The organic phase was separated, washed with brine (5×6 mL), dried (Na$_2$SO$_4$) and concentrated to dryness. The crude material was purified on a silica gel column with a mixture of 10% ethyl acetate in toluene as eluent. Evaporation of the appropriate fractions gave 0.56 g, 70% of the title compound as a yellow syrup; ir (neat) $v_{max}$: 1763 (C=O of β-lactam), 1655 (C=O of ester), 1610 (C=C of enol), 1240 (CH$_3$Si) cm$^{-1}$; $^1$Hmr (CDCl$_3$) δ: 0.05 and 0.09 (2s, CH$_3$Si), 0.087 (m, t-butyl-Si), 1.18 (t, J=7.3 Hz, $\underline{CH_3}$CH$_2$C(OH)=C), 1.29 (d, J=6.3 Hz, $\underline{CH_3}$CHOSi), 2.43 (q, J=7.3 Hz, CH$_3$$\underline{CH_2}$C(OH)=C), 3.16 (dd, J=2.7 Hz, J=4.5 Hz, H-3), 3.57 (s, CH$_3$O), 4.25 (m, CH$_3$$\underline{CH}$OSi), 5.34 (d, J=2.7 Hz, H-4), 7.1-7.4 (m, phenyl). Anal. calcd. for C$_{23}$H$_{35}$NO$_5$SSi: C 59.32, H, 7.58, N 3.01, S 6.89; found: C 59.23, 7.83, N 2.91, S 7.03.

EXAMPLE 8

Preparation of 2-chloroallyl 2-[(3S,4R) 3-(1R-t-butyldimethylsilyloxyethyl)-2-oxo-4-phenylthio-1-azetidinyl]-3-hydroxycrotonate

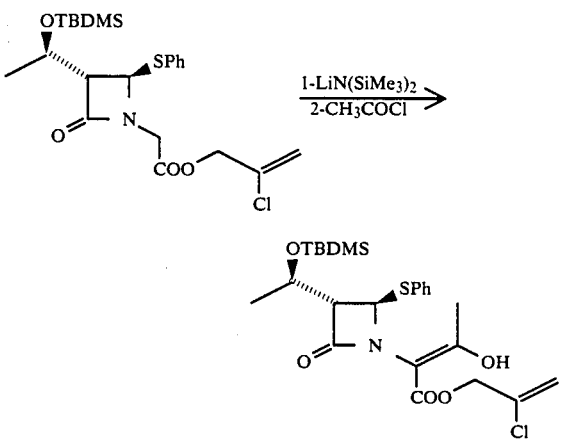

To a cold (−70° C.) solution of 2-chloroallyl 2-[(3S,4R) 3-(1R-t-butyldimethylsilyloxyethyl)-2-oxo-4-phenylthio-1-azetidinyl] acetate (0.342 g, 0.73 mmol) in dry tetrahydrofuran (2 mL) kept under a nitrogen atmosphere was added a solution of lithium bis(trimethylsilyl)amide in tetrahydrofuran (1.6 mL, 1M, 1.6 mmol). The mixture was stirred for 15 minutes and treated with acetyl chloride (0.054 mL, 0.76 mmol). The stirring was continued for 0.75 hour before diluting with dichloromethane (25 mL). The organic solution was washed with water (5 mL) and brine, dried (MgSO$_4$), and concentrated to dryness. The crude material was chromatographed on a silica gel column with a mixture of 10% ethyl acetate in toluene as eluting solvent. The appropriate fractions were concentrated to give 0.22 g, 59%, of a yellow syrup; ir (neat) $v_{max}$: 1765 (C=O), 1255 (CH$_3$Si) cm$^{-1}$; $^1$Hmr (CDCl$_3$) δ: 0.07 (m, CH$_3$Si), 0.87 (m, t-butyl-Si), 1.31 (d, J=6.2 Hz, $\underline{CH_3}$CHOSi), 3.18 (dd, J=2.6 Hz, J=5.5 Hz, H-3), 7.1-7.6 (m, phenyl): Anal. calcd. for C$_{24}$H$_{34}$NO$_5$SSiCl: C 56.29, H 6.69, N 2.73, S 6.26, Cl 6.92; found C 56.24, H 6.93, N 2.75, S 6.26, Cl 6.92.

EXAMPLE 9

Preparation of allyl 2-[(3S,4R) 3-(1R-t-butyldimethylsilyloxyethyl)-4-methylthio-2-oxo-1-azetidinyl]-3-hydroxycrotonate

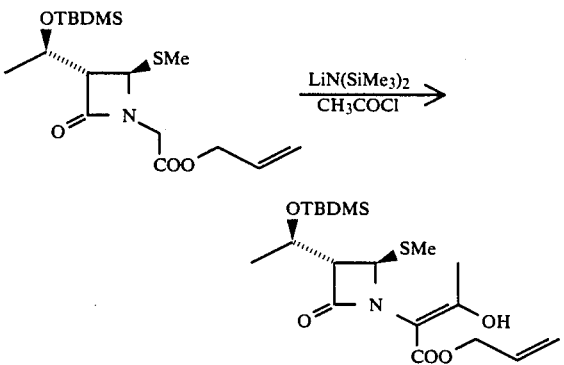

To a cold (−78° C.) solution of lithium bis(trimethylsilyl)amide [prepared from 1,1,1,3,3,3-hexamethyldisilazane (6.03 mL, 28.6 mmol) and n-butyllithium (11.4 mL, 1.55M, 17.7 mmol)] in dry tetrahydrofuran (60 mL) kept under a nitrogen atmosphere was added a solution of allyl 2-[(3S,4R) 3-(1R-t-butyldimethylsilyloxyethyl)-4-methylthio-2-oxo-1-azetidinyl]-acetate (3.16 g, 8.46 mmol) in dry tetrahydrofuran (20 mL). The mixture was stirred for 15 minutes, treated with acetyl chloride (0.60 mL, 8.4 mmol), stirred for 35 minutes and, diluted with water (50 mL) containing acetic acid (0.38 mL, 6.6 mmol) and dichloromethane (400 mL). The organic layer was separated, washed with brine (5×100 mL), dried (MgSO4) and concentrated to dryness; 5.4 g. The crude material was purified on a silica gel (100 g) column with a mixture of 2% of ethyl acetate in dichloromethane as eluting solvent. Evaporation of the appropriate fractions gave 2.07 g, 58.9% of the title compound; ir (neat) $v_{max}$: 1760 (C=O of β-lactam), 1650 (C=O of ester), 1610 (C=C of enol) and 1240 (CH3Si) cm$^{-1}$; $^1$Hmr (CDCl3) δ: 0.06, 0.09 (2s, CH3Si), 0.88 (m, t-butyl-Si), 1.28 (d, J=6.1 Hz, CH3CHOSi), 2.13 (s, CH3S, CH3C(OH=C), 3.09 (dd, J=2.5 Hz, J=5.6 Hz, H-3), 4.2 (m, CH3CHOSi) 4.7 (m, CH2CH=CH2), 4.95 (d, J=2.5 Hz, H-4), 5.1–5.5 (m, CH2CH=CH2), 5.6–6.2 (m, CH2CH=CH2); uv (CH3CN) $\lambda_{max}$: 264 (ε5989); Anal. calcd. for C19H33NO5SSi; C 54.90, H 8.00, N 3.37, S 7.71; found: C 54.69, H 8.30, N 3.25, S 7.60.

Example 10 illustrates the combined conversion of Steps (C) and (D).

EXAMPLE 10

Preparation of 2-chloroallyl 2-[(3S,4R) 3-(1R-t-butyldimethylsilyloxyethyl)-2-oxo-4-phenylthio-1-azetidinyl]-3-methylsulfonyloxycrotonate

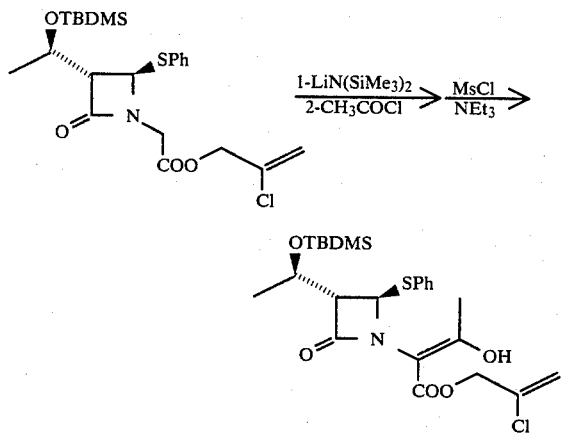

To a cold (−70° C.) solution of 2-chloroallyl 2-[(3S,4R) 3-(1R-t-butyldimethylsilyloxyethyl)-2-oxo-4-phenylthio-1-azetidinyl]acetate (1.62 g, 3.4 mmol) in dry tetrahydrofuran (10 mL) kept under a nitrogen atmosphere was added dropwise (5 minutes) a solution of lithium bis(trimethylsilyl)amide in tetrahydrofuran (7.1 mL, 1M, 7.1 mmol). The mixture was stirred at −70° C. for 20 minutes, treated dropwise (5 minutes) with acetyl chloride (0.25 mL, 3.5 mmol) and stirred for 40 minutes. The cooling bath was removed and the mixture was diluted with dichloromethane (130 mL) containing acetic acid (0.40 mL, 6.9 mmol), stirred for 5 minutes and treated with water (25 mL). The resulting mixture was stirred for a few minutes while the pH was adjusted to 6.3 with acetic acid. The two phases were separated and the organic layer was washed with brine (2×10 mL), dried (MgSO4) and concentrated to dryness. The crude 2-chloroallyl 2-[(3S,4R) 3-(1R-t-butyldimethylsilyloxyethyl)-2-oxo-4-phenylthio-1-azetidinyl]-3-hydroxycrotonate was dissolved in dichloromethane (16 mL), cooled to 0° C. under a nitrogen atmosphere and treated with triethylamine (0.62 mL, 4.4 mmol) and methanesulfonyl chloride (0.32 mL, 4.1 mmol). The mixture was stirred at 0° C. for 1 hour and then diluted with dichloromethane (75 mL). The organic solution was washed with cold (0° C.) water (3×10 mL) and brine, dried (Na2SO4) and concentrated to dryness. The crude material was chromatographed on a silica gel column with a mixture of 0–2% ethyl acetate in toluene as eluting solvent. The appropriate fractions were concentrated to give a yellow syrup, 0.43 g, 21%. The analytical data were identical to the compound prepared from 2-chloroallyl 2-[(3S,4R)3-(1R-t-butyldimethylsilyloxyethyl)-2-oxo-4-phenylthio-1-azetidinyl]-3-hydroxycrotonate in Example 12.

Examples 11–13 each illustrate the conversion of Step (D).

EXAMPLE 11

Preparation of methyl 2-[(3S,4R)-3-(1R-t-butyldimethylsilyloxyethyl)-2-oxo-4-phenylthio-1-azetidinyl]-3-ethyl-3-methylsulfonyloxyacrylate (E/Z mixture)

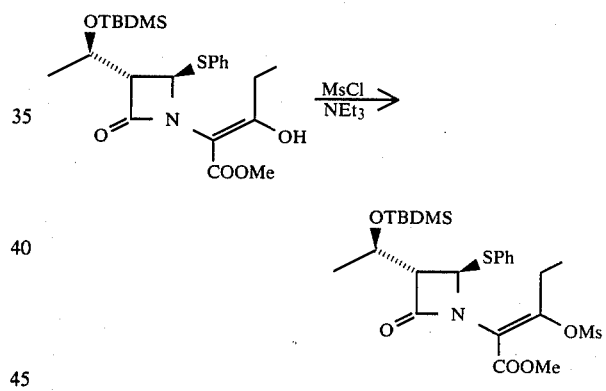

To a cold (0° C.) mixture of methyl 2-[(3S,4R) 3-(1R-t-butyldimethylsilyloxyethyl)-2-oxo-4-phenylthio-1-azetidinyl]-3-ethyl-3-hydroxylate (0.51 g, 1.1 mmol) and triethylamine (0.24 mL, 1.72 mmol) in dichloromethane (6 mL) kept under a nitrogen atmosphere was added dropwise methanesulfonyl chloride (0.13 mL, 1.68 mmol). The reaction mixture was stirred at 0° C. for 1.5 hour, diluted with dichloromethane (15 mL), washed with cold (0° C.) water (2×6 mL) and brine, and dried (Na2SO4). The solvent was evaporated under reduced pressure leaving a crude material which was purified on a silica gel column. Evaporation of the appropriate fractions gave a yellow syrup, 0.52 g, 87%. The title compound was obtained as a mixture of E/Z isomers; ir (neat) $v_{max}$: 1768 (C=O of β-lactam), 1730 (C=O of ester), 1628 (C=C of the enolmesylate), 1370 and 1248 (sulfonate) cm$^{-1}$; $^1$Hmr (CDCl3) δ: 0.05 and 0.09 (2s, CH3Si), 0.88 (m, t-butyl-Si), 1.0–1.4 (CH3CHOSi, CH3CH2C(OMs)=C), 2.54 (q, J=7.3 Hz, CH3CH2C(OMs)=C, 3.00 (q, J=7.3 Hz, CH3CH2C(OMs)=C), 3.19 and 3.24 (2s, CH3SO3), 3.53 and 3.55 (2s, CH3O), 4.25 (m, CH3CHOSi), 5.44, (d, J=2.9 Hz, H-4), 5.50 (d=2.9 Hz, H-4), 7.1–7.6 (m, phenyl).

EXAMPLE 12

Preparation of 2-chloroallyl 2-[(3S,4R) 3-(1R-t-butyldimethylsilyloxyethyl)-2-oxo-4-phenylthio-1-azetidinyl]-3-methylsulfonyloxycrotonate

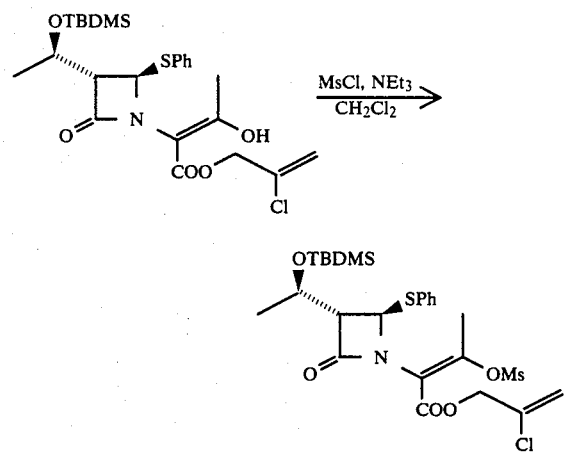

To a cold (0° C.) solution of 2-chloroallyl 2-[(3S,4R) 3-(1R-t-butyldimethylsilyloxyethyl)-2-oxo-4-phenylthio-1-azetidinyl]-3-hydroxycrotonate (0.22 g, 0.43 mmol) in dichloromethane (3 mL) was added triethylamine (0.078 mL, 0.56 mmol) and methanesulfonyl chloride (0.040 mL, 0.52 mmol). The mixture was stirred at 0° C. for 1 hour and diluted with dichloromethane (7 mL). The organic solution was washed with water (2×3 mL) and brine, dried (MgSO4) and concentrated to dryness. The crude material was purified by preparative tlc (10% ethylacetate in toluene) to give a yellow syrup; 0.092 g, 36%; ir (neat) ν$_{max}$: 1765 (C=O of β-lactam), 1730 (C=O of ester), 1635 (C=C of enol mesylate), 1360 (sulfonate) cm$^{-1}$, $^1$Hmr (CDCl3) δ: 0.09 (m, CH3Si), 0.88 (m, t-butyl-Si), 1.29 and 1.31 (2d, J=6.2 Hz, CH3CHOSi), 2.21 and 2.64 (2s, CH3C(OMs)=C), 3.06 (dd, J=2.8 Hz, J=5.3 Hz, H-3), 3.17 and 3.22 (2s, CH3SO3), 4.25 (m, CH3CHOSi), 4.5 (m, COOCH2C(Cl)=CH2), 5.3–5.6 (m, COOCH2C-(Cl)=CH2, H-4), 7.2–7.8 (m, phenyl). Anal. calcd. for C25H36NO7S2SiCl: C 50.87, H 6.15, N 2.37, S. 10.86; found: C 51.33, H 6.07, N 2.17, S 10.65.

EXAMPLE 13

Preparation of allyl 2-[(3S,4R) 3-(1R t-butyldimethylsilyloxyethyl)-4-methylthio-2-oxo-1-azetidinyl]-3-methylsulfonyloxycrotonate

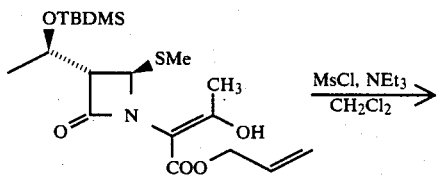

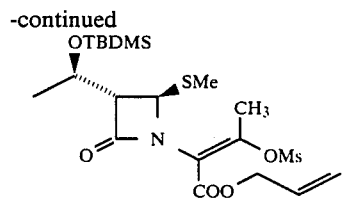

To a cold (0° C.) solution of allyl 2-[(3S,4R) 3-(1R-t-butyldimethylsilyloxyethyl)-4-methylthio-2-oxo-1-azetidinyl]-3-hydroxycrotonate (0.159 g, 0.38 mmol) in dichloromethane (2 mL) was added triethylamine (0.064 mL, 0.46 mmol) and methanesulfonylchloride (0.033 mL, 0.43 mmol). The mixture was stirred at 0° C. for 40 minutes and diluted with dichloromethane. The organic solution was washed with water (2×2 mL) and brine, dried (Na2SO4) and concentrated to dryness; 0.174 g, 93%. A purification by preparative tlc afforded an analytical sample; ir (neat) ν$_{max}$: 1765 (C=O of β-lactam), 1724 (C=O of ester), 1635 and 1645 (C=C of enol mesylate), 1365 and 1250 (sulfonate) cm$^{-1}$; $^1$Hmr (CDCl3) δ: 0.06 and 0.08 (2s, CH3Si), 0.83 (m. t-butyl-Si), 1.27 (d, J=6.3 Hz, CH3CHOSi), 2.13 and 2.15 (2s, CH3S, E and Z isomers), 2.31 and 2.63 (2s, CH3C(OMs)=C, E and Z isomers), 3.23 and 3.25 (2s, CH3SO3, E and Z isomers), 4.2 (m, CH3CHOSi), 4.5–4.8 (m, CH2CH=CH2, 5.21 (d, J=2.7 Hz, H-4), 5.1–5.5 (m, CH2CH=CH2), 5.6–6.3 (m, CH2CH=CH2). Anal. calcd. for C20H35NO7S2Si: C 48.66, H 7.15, N 2.84, S 12.99; found C 48.56, H 6.93, N 3.07, S 12.68.

Examples 14 and 15 each illustrate the conversion of Step (E-1).

EXAMPLE 14

Preparation of methyl 2-[(3S,4R) 3-(1R-t-butyldimethylsilyloxyethyl)-4-chloro-2-oxo-1-azetidinyl]-3-methylsulfonyloxycrotonate

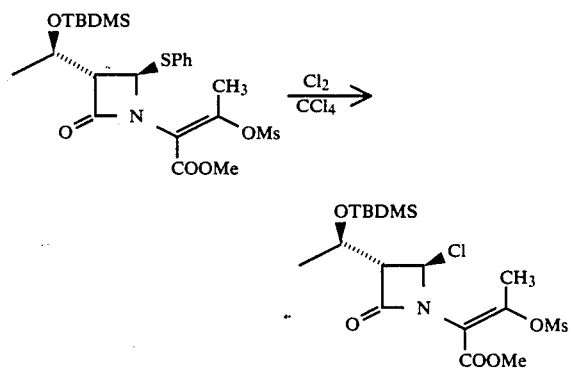

To a cold (−70° C.) solution of a E/Z mixture of methyl 2-[(3S,4R)3-1R-t-butyldimethylsilyloxyethyl)-2-oxo-4-phenylthio-1-azetidinyl]-3-methylsulfonyloxycrotonate (0.10 g, 0.188 mmol) in dichloromethane (4.5 mL) kept under a nitrogen atmosphere was added a solution of chlorine in carbon tetrachloride (0.157 mL, 1.22M, 0.191 mmol). The mixture was stirred for 5 minutes and kept under high vacuum for 0.5 hour while it was warmed up to 23° C. The resulting crude mixture was purified by preparative tlc (10% ethyl acetate in toluene) to give the title compound as an E/Z mixture, 0.063 g, 73%; ir (neat) ν$_{max}$: 1780 (C=O β-lactam), 1728 (C=O of ester) and 1636 (C=C of enol mesylate) cm$^{-1}$; $^1$Hmr (CDCl$_3$) δ: 0.05 and 0.08 (2s, CH$_3$Si), 0.087 (m, t-butyl-Si), 1.30 (d, J=6.3 HZ, C$\underline{H}_3$ CHOSi), 2.31 and 2.68 (2s, CH$_3$C(OMs)=C) 3.24 and 3.26 (s, CH$_3$SO$_2$), 3.41 (m, H-3), 3.80 and 3.82 (s, CH$_3$O), 4.2 (m, CH$_3$C$\underline{H}$OSi), 5.97 (m, H-4). Anal. calcd. for C$_{17}$H$_{30}$ClNO$_7$SSi: C 44.77, H 6.63, N 3.07; found: C 44.99, H 6.53, N 2.98.

Example 15

Preparation of allyl 2-[(3S,4R) 3-(1R-t-butyldimethylsilyloxyethyl)-4-chloro-2-oxo-1-azetidinyl]-3-methylsulfonyloxycrotonate (E/Z mixture)

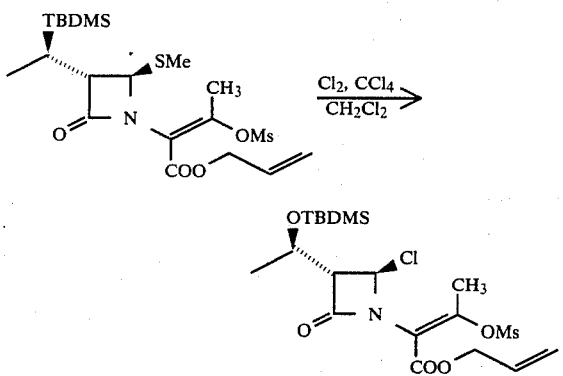

To a cold (−70° C.) solution of E/Z mixture of allyl 2-[(3S,4R) 3-(1R-t-butyldimethylsilyloxyethyl)-4-methylthio-2-oxo-1-azetidinyl]-3-methylsulfonyloxycrotonate (0.089 g, 0.18 mmol) in dichloromethane (1.2 mL) kept under a nitrogen atmosphere was added a solution of chlorine in carbon tetrachloride (0.16 mL, 1.22M, 0.20 mmol). The mixture was stirred at −70° C. for 2 hours, pumped under vacuum (100μ) for 40 minutes and treated with saturated NaHCO$_3$ solution (0.8 mL) and methanol (0.05 mL). The organic layer was separated, washed with cold (0° C.) water, dried (Na$_2$SO$_4$) and concentrated to dryness; 0.095 g. The crude material was purified by preparative tlc to give the title compound as a pale yellow syrup; ir (neat) ν$_{max}$: 1780 (C=O of β-lactam), 1725 (C=O of ester), 1635 (C=C of enol mesylate), 1365 and 1258 (sulfonate) cm$^{-1}$; $^1$Hmr (CDCl$_3$) δ: 0.07 (m, CH$_3$Si), 0.86 (m, t-butyl-Si), 3.25 (s, CH$_3$SO$_3$), 3.41 (dd, J=1.5 Hz, J=5.2 Hz, H-3), 4.2 (m, CH$_3$C$\underline{H}$OSi), 4.5-4.8 (m, C$\underline{H}_2$CH=CH$_2$), 5.1-5.5 (m, CH$_2$CH=C$\underline{H}_2$), 5.6-6.2 (m, CH$_2$C$\underline{H}$=CH$_2$), 5.97 (d, J=1.5 Hz, H-4) and 2,3-dichloropropyl 2-[(3S,4R)3-(1R-t-butyldimethylsilyloxyethyl)-4-chloro-2-oxo-1-azetidinyl]-3-methylsulfonyloxycrotonate; ir (neat) ν$_{max}$: 1780 (C=O of β-lactam), 1730 (C=O of ester), 1635 (C=O of enol mesylate), 1365 and 1255 (sulfonate) cm$^{-1}$; $^1$Hmr (CDCl$_3$) δ: 0.07 (m, CH$_3$Si), 0.86 (m, t-butyl-Si), 1.31 (d, J=6.3 Hz, C$\underline{H}_3$CHOSi), 2.33 and 2.68 (2s, CH$_3$C(OMs)=C), 3.25 and 3.28 (2s, CH$_3$SO$_3$), 3.3-3.5 (m, H-3), 5.95 (m, H-4); uv (CH$_3$CN) λ$_{max}$: 244 (ε 6865). Anal. calcd. for C$_{19}$H$_{32}$NO$_7$SSiCl$_3$: C 41.27, H 5.83, N 2.53, S 5.80, Cl 19.23; found: C 41.42 H 5.84, N 2.46, S 5.83, Cl 18.63.

Examples 16-18 each illustrate the combined conversion of Steps (E-1) and (E-2).

EXAMPLE 16

Preparation of methyl 2-[(3S,4R) 3-(1R-t-butyldimethylsilyloxyethyl)-4-chloro-2-oxo-1-azetidinyl]-3-ethyl-3-phenylthioacrylate (E/Z mixture)

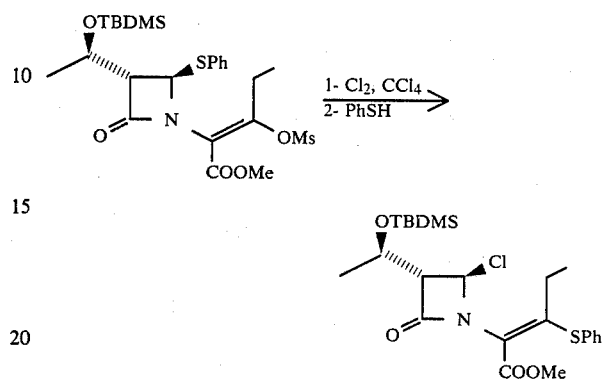

To a cold (−70° C.) solution of methyl 2-[(3S,4R) 3-(1R-t-butyldimethylsilyloxyethyl)-2-oxo-4-phenylthio-1-azetidinyl]-3-ethyl-3-methylsulfonyloxyacrylate (E,Z mixture, 0.476 g, 0.88 mmol) in dichloromethane (23 mL) kept under a nitrogen atmosphere was added a solution of chlorine in carbon tetrachloride (0.73 mL, 1.22M, 0.89 mmol). The mixture was stirred at −70° C. for 7 minutes and the excess of chlorine was removed under high vacuum at −70° C. for 40 minutes. The resulting solution was treated with diisopropylethylamine (0.335 mL, 1.9 mmol) and a solution of thiophenol (0.189 mL, 1.8 mmol) in acetonitrile (5 mL), warmed up to 23° and stirred for 1 hour. The dichloromethane was evaporated and the mixture was treated with diisopropylethylamine (0.050 mL, 0.29 mmol) and thiophenol (0.028 mL, 0.27 mmol), stirred for 2 hours at 23° C. and diluted with ethylacetate (50 mL). The organic solution was washed with water (2×10 mL) and brine, dried (MgSO$_4$) and concentrated to dryness. The crude material (0.63 g) was chromatographed on a silica gel column with a mixture of 5-15% of ether in petroleum ether as eluting solvent. Evaporation of the appropriate fractions gave 0.283 g, 66.4%; isomer A: ir (neat) λ$_{max}$: 1780 (C=O of β-lactam), 1708 (C=O of ester); $^1$Hmr (CDCl$_3$) δ: 0.08 and 0.10 (2s, CH$_3$Si), 0.89 (m, t-butyl-Si), 0.94 (t, J=7.3 Hz, CH$_3$C$\underline{H}_2$C(SPh)=C), 1.32 (d, J=6.1 Hz, CH$_3$C$\underline{H}$OSi), 2.38 (m, C$\underline{H}_3$CH$_2$C(SPh)=C), 3.41 (dd, J=1.5 Hz, J=6.0 Hz, H-3), 3.82 (s, CH$_3$O), 4.23 (CH$_3$C$\underline{H}$OSi), 5.86 (d, J=1.5 Hz, H-4), 7.1-7.6 (m, phenyl); uv (CH$_3$CN) λ$_{max}$: 294 (ε 13,315); [α]$_D^{23}$ −92.8 (c 0.35, CHCl$_3$); isomer C: ir (neat) ν$_{max}$: 1780 (C=O of β-lactam), 1708 (C=O of ester) cm$^{-1}$; $^1$Hmr (CDCl$_3$), δ: 0.09 (s, CH$_3$Si), 0.88 (m, t-butyl-Si), 1.03 (t, J=7.1 Hz, CH$_3$C$\underline{H}_2$C(SPh)=C), 1.32 (d, J=6.2 Hz, CH$_3$C$\underline{H}$OSi), 2.57 (m, C$\underline{H}_3$CH$_2$C(SPh)=C), 3.50 (dd, J=1.5 Hz, J=5.1 Hz, H-3), 3.78 (s, CH$_3$O), 4.24 (m, CH$_3$CHOSi), 6.10 (d, J=1.5 Hz, H-4), 7.1-7.6 (m, phenyl); uv (CH$_3$CN) λ$_{max}$: 295 (ε 13,226); [α]$_D^{23}$ +5 (c 1.6, CHCl$_3$). Anal. calcd. for C$_{23}$H$_{34}$NO$_4$SSiCl: C 57.06 H 7.08, N 2.87, S 6.62, Cl 7.32; found C 65.89, H 7.07, N 2.84, S 6.89, Cl 7.35.

EXAMPLE 17

Preparation of 2-chloroallyl 2-[(3S,4R) 3-(1R-t-butyldimethylsilyloxyethyl)-4-chloro-2-oxo-1-azetidinyl]-3-phenylthiocrotonate

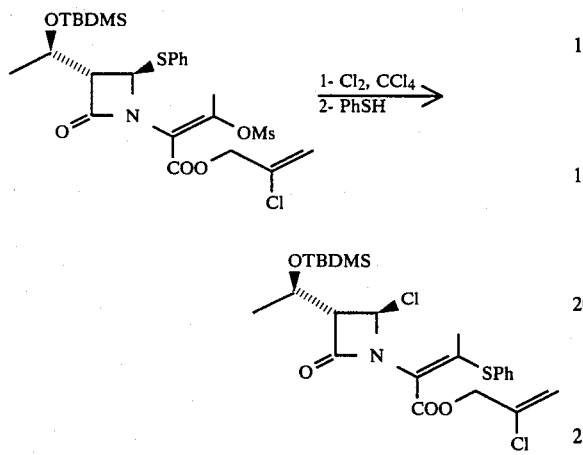

To a cold (−70° C.) solution of E/Z mixture of 2-chloroallyl 2-[(3S,4R) 3-(1R-t-butyldimethylsilyloxyethyl)-2-oxo-4-phenylthio-1-azetidinyl]-3-methylsulfonyloxycrotonate (0.048 g, 0.08 mmol) in dichloromethane (3 mL) kept under a nitrogen atmosphere was added a solution of chlorine in carbon tetrachloride (0.068 mL, 1.22M, 0.083 mmol). The mixture was stirred at −70° C. for 7 minutes and the excess of chlorine was removed at −70° C. under high vacuum for 25 minutes. The resulting mixture was treated with diisopropylethylamine (0.031 mL, 0.18 mmol) and a solution of thiophenol (0.018 mL, 0.17 mmol) in acetonitrile (0.5 mL). The cooling bath was removed and the stirring was continued for 0.5 hour. The dichloromethane was evaporated and the resulting solution was stirred for 0.75 hour and diluted with ethyl acetate (5 mL). The organic solution was washed with water (2×1 mL) and brine, dried ($Na_2SO_4$) and concentrated to dryness. The crude material was purified by preparative tlc with a mixture of 30% ether in petroleum ether as eluting solvent and the title compound was obtained as a yellow syrup; 0.028 g, 65%; it was isolated as a mixture of E/Z isomer; ir (neat) $v_{max}$: 1783 (C=O of β-lactam), 1713 (C=O of ester) $cm^{-1}$; $^1$Hmr (CDCl$_3$) δ: 0.07 (m, CH$_3$Si), 0.88 (m, t-butyl-Si), 1.31 and 1.34 (2d, J=6.3 Hz, CH$_3$CHOSi), 1.93 and 2.24 (2s, CH$_3$C(SPh)=C), 3.41 and 3.52 (2dd, J=1.5 Hz, J=5.6 Hz, H-3), 4.25 (m, CH$_3$CHOSi), 4.4–5.0 (m, COOCH$_2$C(Cl)=CH$_2$), 5.3–5.6 (m, COOCH$_2$C(Cl)=CH$_2$), 5.94 and 6.12 (2d, J=1.5 Hz, H-4), 7.2–7.6 (m, phenyl); Anal. calcd. for $C_{24}H_{33}NO_4SSiCl_2$: C 54.33, H 6.27, N 2.64, S 6.04, Cl 13.36; found: C 54.22, H 6.47, N 2.54, S 6.19, Cl 13.29.

EXAMPLE 18

Preparation of 2-chloroallyl 2-[(3S,4R) 3-(1R-t-butyldimethylsilyloxyethyl)-4-chloro-2-oxo-1-azetidinyl]-3-methylthiocrotonate (E,Z mixture)

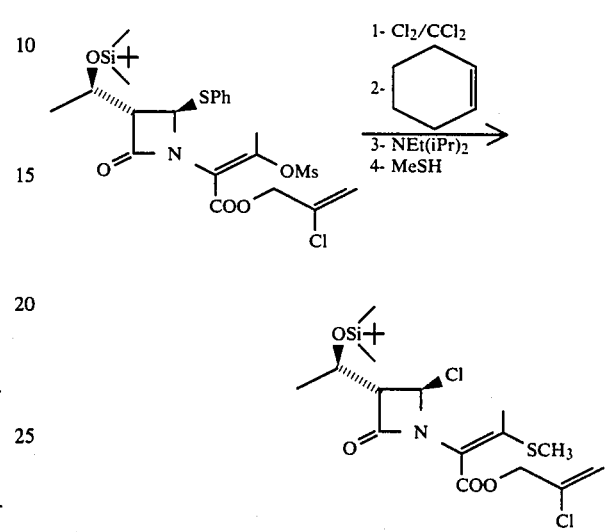

To a cold (−70° C.) solution of E,Z mixture of 2-chloroallyl 2-[(3S,4R) 3-(1R-t-butyldimethylsilyloxyethyl)-2-oxo-4-phenylthio-1-azetidinyl]-3-methylsulfonyloxycrotonate (0.23 g, 0.39 mmol) in dichloromethane (80 mL) kept under a nitrogen atmosphere are added a solution of chlorine in carbon tetrachloride (0.73 mL, 0.55M, 0.40 mmol). The mixture was stirred for 7 minutes at −70° C., pumped under high vacuum for 25 minutes, treated with cyclohexene (0.042 mL, 0.41 mmol), warmed up to −30° C., stirred for 30 minutes. at −30° C., cooled down to −70° C. and treated successively with diisopropylethylamine (0.15 mL, 2.86 mmol) and methanethiol (0.045 mL, 0.81 mmol) in acetonitrile (3 mL). The cooling bath was removed and the mixture was stirred for 1 hour at 23° C., pumped under vacuum and diluted with ethylacetate (30 mL). The organic solution was washed with water (2×6 mL) and brine, dried ($Na_2SO_4$) and concentrated to dryness. The crude material was purified by preparative tlc with a mixture of 30% ether in petroleum ether as eluting solvent to give a yellow syrup; 0.11 g, 60%; ir (neat) $v_{max}$: 1780 (C=O of β-lactam), 1700 (C=O of ester) $cm^{-1}$; $^1$Hrm (CDCl$_3$) δ: 0.09 (m, CH$_3$Si), 0.88 (m, t-butyl-Si), 1.32 (d, J=6.2 Hz, CH$_3$CHOSi), 2.29 and 2.60 (2s, CH$_3$C(SCH$_3$)=C), 2.39 (s, CH$_3$S), 3.3–3.5 (m, H-3), 4.22 (m, CH$_3$CHOSi), 4.4–5.0 (m, COOCH$_2$(Cl)=CH$_2$), 5.2–5.6 (m, COOCH$_2$C(Cl)=CH$_2$), 5.90 and 6.00 (2d, J=1.4 Hz, H-4). Anal. calcd for $CH_{19}H_{31}NO_4SSiCl_2$: C 48.71, H 6.67, N 2.99; found: C 48.71, H 6.81, N 2.99.

Example 19 illustrates the conversion of Step (E-2).

EXAMPLE 19

Preparation of methyl 2-[(3S,4R) 3-(1R-t-butyldimethylsilyloxyethyl)-4-chloro-2-oxo-1-azetidinyl]-3-(pyridin-2-ylmethylthio)crotonate

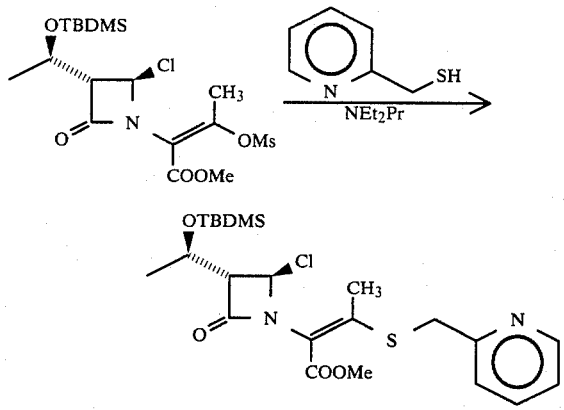

To a cold (0° C.) solution of E/Z mixture of methyl 2-[(3S,4R) 3-(1R-t-butyldimethylsilyloxyethyl)-4-chloro-2-oxo-1-azetidinyl]-3-methylsulfonyloxycrotonate (0.063 g, 0.138 mmol) in dry acetonitrile (0.5 mL) kept under a nitrogen atmosphere was added diisopropylethylamine (0.024 mL, 0.138 mmol) followed by the dropwise addition of a solution of 2-picolythiol (0.019 g, 0.152 mmol) in acetonitrile (0.2 mL). The mixture was stirred at 0° C. for 4 hours and diluted with ethyl acetate (3.5 mL). The organic solution was washed with cold water (2×0.75 mL) and brine, dried (MgSO4) and concentrated to dryness (0.061 g). The crude mixture was chromatographed on silica gel column (4.0 g) with a mixture of 33% of petroleum ether in ether to give the title compound as a E/Z mixture, 0.030 g, 44.8%; ir (neat) $\nu_{max}$: 1778 (C=O of β-lactam), 1709 (C=O of ester), 1695 and 1675 cm$^{-1}$; $^1$Hmr (CDCl3) δ: 0.05 and 0.07 (2s, CH3Si), 0.86 (m, t-butyl-Si), 1.31 (d, J=6.3 Hz, CH3CHOSi), 2.32 and 2.57 (2s, CH3C(SCH2Py)=C), 3.46 (dd, J=1.5 Hz, J=5.3 Hz, H-3 of Z isomer), 3.73 and 3.76 (2s, CH3O), 4.0–4.4 (m, CH3CHOSi, SCH2), 5.87 and 5.97 (2d, J=1.5 Hz, H-4), 7.0–7.8 (m, pyridine), 8.4–8.6 (m, pyridine); uv (CH3CN) $\lambda_{max}$: 295 (ε 13980). Anal. calcd. for C22H33ClN2O4SSi: C 54.47, H 6.86, N 5.77, S 6.61; found: C 54.49, H 6.78, N 5.64, S 6.62 and a E/Z (83/17) mixture of the starting material, 0.009 g, 14%.

Example 20 illustrates the conversion of Step (E-3).

EXAMPLE 20

Preparation of (5R,6S) 2-chloroallyl 6-(1R-t-butyldimethylsilyloxyethyl)-7-oxo-3-phenylthio-1-azabicyclo[3.2.0]hept-2-ene-2-carboxylate

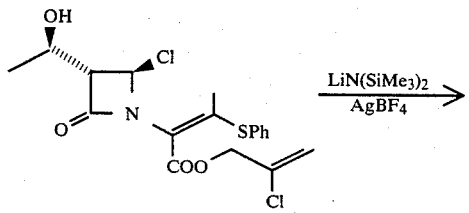

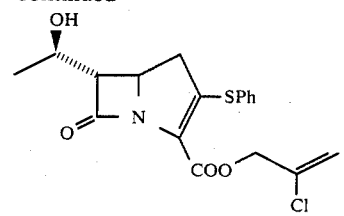

A cold (−65° C.) solution of E/Z mixture of 2-chloroallyl 2-[(3S,4R) 3-(1R-t-butyldimethylsilyloxyethyl)-4-chloro-2-oxo-1-azetidinyl]-3-phenylthiocrotonate (0.055 g, 0.10 mmol) in dry tetrahydrofuran (2.2 mL) kept under a nitrogen atmosphere was treated with a solution of lithium bis(trimethylsilyl)amide in tetrahydrofuran (0.106 mL, 1M, 0.106 mmol). The mixture was stirred at −65° C. for 25 minutes, treated with a solution of silver tetrafluoroborate in tetrahydrofuran (1.03 mL, 0.2M, 0.206 mmol), stirred for 10 minutes at −65° C. and diluted with ethyl acetate (20 mL) containing acetic acid (6 μl, 0.11 mmol). The organic solution was washed with water (2×2 mL) while the pH was adjusted to 7.0 by the addition of acetic acid and brine, dried (MgSO4) and concentrated to dryness. The crude material was purified by preparative tlc (50% ether in petroleum ether) to give the non-reactive Z isomer of the starting material, 0.014 g, 25%; $^1$Hmr (CDCl3): δ: 0.7 (m, CH3Si), 0.87 (m, t-butyl-Si), 1.31 (d, J=6.2 Hz, CH3,CHOSi), 1.93 (s, CH3C(SPh)=C), 3.41 (dd, J=6.2 Hz, J=1.5 Hz, H-3), 4.25 (m, CH3CHOSi), 4.81 (center of ABq, $J_{a,b}$=13.5 Hz, COOCH2C(Cl)=CH2), 5.5 (m, COOCH2C(Cl)=CH2, 5.94 (d, J=1.5 Hz, H-4), 7.2–7.7 (m, phenyl), uv (CH3CN) $\lambda_{max}$: 295 (ε 12279), $[\alpha]_D^{25}$ −52.1° (c 1.4, CHCl3), and the title compound; 0.009 g, 18%; ir (neat) $\nu_{max}$: 1780 (C=O of β-lactam), 1725, 1710 cm$^{-1}$; $^1$Hmr (CDCl3): 0.07 (m, CH3Si), 0.84 (m, t-butyl-Si), 1.16 (d, J=6.3 Hz, CH3CHOSi), 2.63 ('d', J=9.4 Hz, H-4), 3.02 (dd, J=2.7 Hz, J=5.3 Hz, H-6), 3.8–4.4 (m, CH3CHOSi, H-5), 4.5–5.2 (m, COOCH2C(Cl)=CH2), 5.3–5.8 (m, COOCH2C(Cl)=CH2), 7.3–7.6 (m, phenyl); uv (CH3) $\lambda_{max}$: 319 (ε12904); $[\alpha]_D^{25}$ +17.1° (c 0.8, CHCl3).

Examples 21 and 22 each illustrate the conversion of Step (E-4).

EXAMPLE 21

Preparation of methyl 2-[(3S,4R) 3-(1R-t-butyldimethylsilyloxyethyl)-2-oxo-4-phenylthio-1-azetidinyl]-3-(pyridin-2-ylmethylthio)crotonate (E/Z mixture)

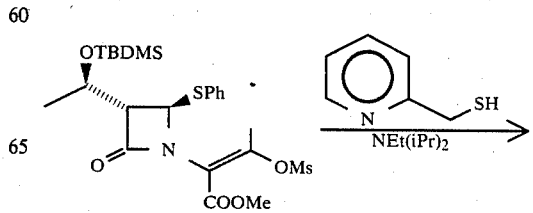

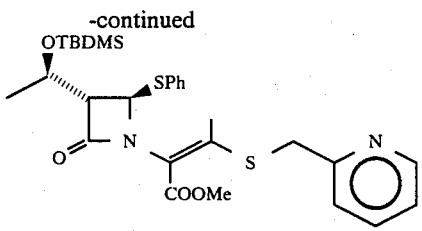

To a solution of E/Z mixture of methyl 2-[(3S,4R) 3-(1R-t-butyldimethylsilyloxyethyl)-2-oxo-4-phenylthio-1-azetidinyl]-3-methylsulfonyloxycrotonate (0.40 g, 0.76 mmol) in dry acetonitrile (4 mL) kept under a nitrogen atmosphere was added diisopropylethylamine (0.14 mL, 0.80 mmol) and 2-picolythiol (0.189 g, 1.51 mmol). The mixture was stirred at 50° C. for 5 hours, cooled to 23° C. and diluted with ethyl acetate (25 mL). The organic solution was washed with water-brine mixture (1:1), dried (MgSO4) and concentrated to dryness. The crude material was chromatographed in a silica gel column (15 g) with a mixture of 30% petroleum ether in ether as eluting solvent. Evaporation of the appropriate fractions gave the title compound as an E/Z mixture; 0.274 g, 65%; ir (neat) $\nu_{max}$: 1762 (C=O of β-lactam), 1709 (C=O of ester), 1590, 1568 cm$^{-1}$; $^1$HMr (CDCl3) δ: 0.06 (m, CH3Si), 0.85 (s, t-butyl-Si), 1.28 and 1.29 (2d, J=6.2 Hz, CH3CHOSi), 2.26 and 2.45 (2s, CH3C(SCH2Py)=C), 3.15 and 3.20 (2dd, J=1.8 Hz, J=5.2 Hz, H-3), 3.49 and 3.51 (2s, CH3O), 3.9–4.5 (m, CH3CHOSi, CH3C(SCH2Py)=C), 5.44 and 5.52 (2d, J=1.8 Hz, H-4), 7.0–7.9 (m, phenyl, m and p-hydrogen on pyridine), 8.4–8.6 (m, o-hydrogen on pyridine). Anal. calcd. for C28H38N2O4S2Si: C 60.18, H 6.85, N 5.01, S 11.47; found: C 59.94, H 7.06, N 5.09, S 11.13.

EXAMPLE 22

Preparation of methyl 2-[(3S,4R) 3-(1R-t-butyldimethylsilyloxyethyl)-2-oxo-4-phenylthio-1-azetidinyl]-3-phenylthiocrotonate (E/Z mixture)

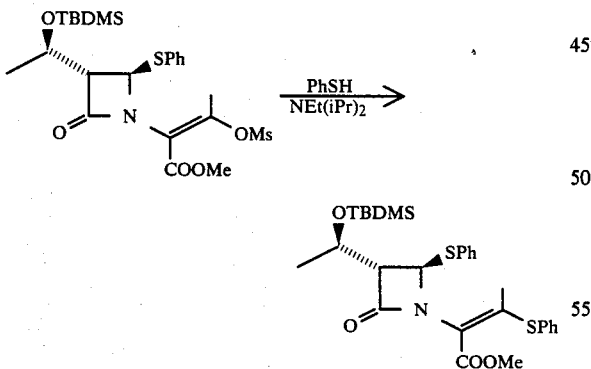

To a solution of an E/Z mixture of methyl 2-[(3S,4R) 3-(1R-t-butyldimethylsilyloxyethyl)-2-oxo-4-phenylthio-1-azetidinyl]-3-methylsulfonyloxycrotonate (0.154 g, 0.29 mmol) in dry acetonitrile (1.5 mL) kept under a nitrogen atmosphere was added diisopropylethylamine (0.056 mL, 0.32 mmol) and thiophenol (0.033 mL, 0.32 mmol). The mixture was stirred at 23° C. for 4 hours, diluted with ethyl acetate (8 mL) and washed with water, diluted NaHCO3 solution, water and brine. The organic solution was dried (Na2SO4) and concentrated to dryness, 0.164 g; the crude material was purified by preparative tlc with a mixture of 50% ether in petroleum ether as eluting solvent to give the title compound, 0.132 g, 84% as a mixture of E/Z isomers; $^1$Hmr (CDCl3) δ: 0.09 (s, CH3Si), 0.87 (s, t-butyl-Si), 1.30 (d, J=6.2 Hz, CH3CHOSi), 1.86 and 2.13 (2s, CH3C(SPh)=C), 3.0–3.4 (m, H-3), 3.55 and 3.60 (2s, CH3O), 4.0–4.5 (m, CH3CHOSi), 5.49 and 5.63 (2d, J=2.8 Hz, J=2.6 Hz, H-4), 7.1–7.8 (m, phenyl).

I claim:

1. A process for preparing a compound of the formula

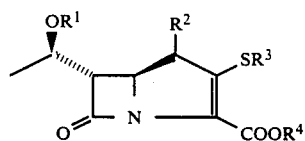

wherein
R$^1$ is hydrogen, or a conventional hydroxy-protecting group, and
R$^2$, R$^3$, and R$^4$ are independently selected from the group consisting of hydrogen; substituted and unsubstituted: alkyl, alkenyl, and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; spirocycloalkyl having 3–6 carbon atoms; phenyl: aralkyl, aralkenyl and aralkynyl wherein the aryl moiety is phenyl and the aliphatic portion has 1–6 carbon atoms; heteroaryl, heteroaralkyl, heterocyclyl and heterocyclylalkyl wherein the hetero atom or atoms in the above-named heterocyclic moieties are selected from the group consisting of 1–4 oxygen, nitrogen and sulfur atoms and the alkyl moieties associated with said heterocyclic moieties have 1–6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1–6 carbon atoms;

which comprises the steps of
(A) reacting a 4,3-disubstituted azetidinone of [the] Formula II

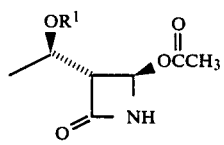

wherein R$^1$ is as defined above, with a solution of an S-nucleophile of the formula R$^5$SH in an organic solvent at −20° C. to 10° C. in the presence of an inorganic base to provide an intermediate of the Formula III

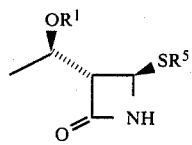   III wherein $R^5$ is a radical selected from the group consisting of hydrogen; substituted and unsubstituted: alkyl, alkenyl, and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; spirocycloalkyl having 3–6 carbon atoms; phenyl; aralkyl, aralkenyl and aralkynyl wherein the aryl moiety is phenyl and the aliphatic portion has 1–6 carbon atoms; heteroaryl, heteroaralkyl, heterocyclyl and heterocyclylalkyl wherein the hetero atom or atoms in the above-named heterocyclic moieties are selected from the group consisting of 1–4 oxygen, nitrogen and sulfur atoms and the alkyl moieties associated with said heterocyclic moieties have 1–6 carbon atoms, and (B) reacting the compound of Formula III with an ester of the formula $BrCH_2CO_2R^4$ in an inert organic solvent at about $-50°$ C. in the presence of an organolithium base and under an inert atmosphere, or at room temperature in the presence of an inorganic base and a tetra-n-butyl-ammonium halide catalyst to provide an intermediate of Formula IV

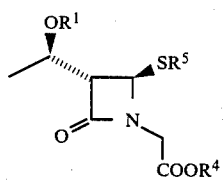   IV wherein $R^1$, $R^4$ and $R^5$ are as defined above;

(C) reacting the compound of Formula IV with an acid chloride of the formula

wherein $R^2$ is as defined above in a reaction inert organic solvent at about $-50°$ C. in the presence of an organolithium base to provide an intermediate of the Formula V

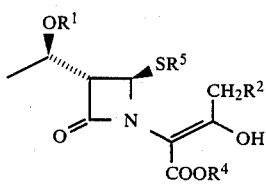   V wherein $R^1$, $R^2$, $R^4$, and $R^5$ are as defined above;

(D) esterifying the compound of Formula V by reaction with methanesulfonyl chloride or toluenesulfonyl chloride to provide a reactive ester of Formula VI

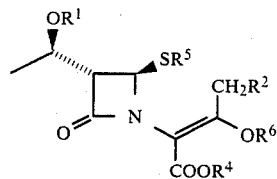   VI wherein $R^6$ is methanesulfonyl, or p-toluenesulfonyl, and $R^1$, $R^2$, $R^4$, and $R^5$, are as defined above; and (E) reacting a solution of the compound of Formula VI in a reaction inert organic solvent at about $-50°$ C. with more than one molecular proportion of chlorine to provide the 4-chloro reactive ester of Formula VIa

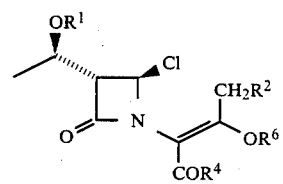   VIa wherein $R^1$, $R^2$, $R^4$, and $R^6$ are as defined above, and thereafter reacting said 4-chloro reactive ester with a thiol of the formula $R^3SH$ in the presence of a tertiary amine to provide the 4-chloro thio-enol ester of Formula VIb

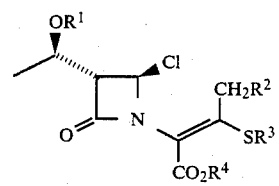   VIb wherein $R^1$, $R^2$, $R^3$, and $R^4$ are as described above, and thereafter causing VIb to cyclize by intramolecular displacement of the 4-chloro group by treatment of thereof in an inert solvent with an organolithium base in the presence of silver tetrafluoroborate, thereby providing the compound of Formula I.

2. The process of claim 1, wherein in Step A the S-nucleophile is thiophenol or methanethiol.

3. The process of claim 1, wherein in Step E the chlorine employed is a solution of chlorine in carbon tetrachloride.

4. The process of claim 1, wherein in Step E $R^3SH$ is 2-picolylthiol, thiophenol, or methanethiol.

5. A process for preparing a compound of the formula

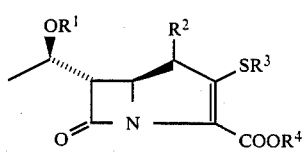   I wherein
$R^1$ is hydrogen, or a conventional hydroxy-protecting group, and $R^2$, $R^3$, and $R^4$ are independently selected from the group consisting of hydrogen; substituted and unsubstituted: alkyl, alkenyl, and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl, aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties have 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms;
which comprises the steps of
(A) reacting a 4,3-disubstituted azetidinone of Formula II

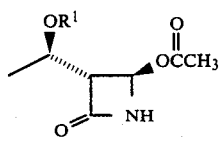

wherein $R^1$ is as defined above, with a solution of an S-nucleophile of the formula $R^5SH$ in an organic solvent at $-20°$ C. to $10°$ C. in the presence of an inorganic base to provide an intermediate of the Formula III

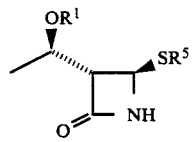

wherein $R^5$ is a radical selected from the group consisting of hydrogen; substituted and unsubstituted: alkyl, alkenyl, and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties have 1-6 carbon atoms, and (B) reacting the compound of Formula III with an ester of the formula $BrCH_2CO_2R^4$ in an inert organic solvent at about $-50°$ C. in the presence of an organolithium base and under an inert atmosphere, or at room temperature in the presence of an inorganic base and a tetra-n-butyl-ammonium halide catalyst to provide an intermediate of Formula IV

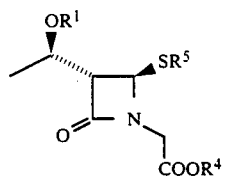

wherein $R^1$, $R^4$ and $R^5$ are as defined above;
(C) reacting the compound of Formula IV with an acid chloride of the formula

wherein $R^2$ is as defined above in a reaction inert organic solvent at about $-50°$ C. in the presence of an organolithium base to provide an intermediate of the Formula V

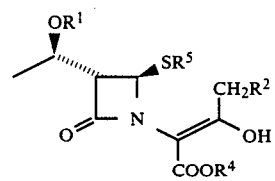

wherein $R^1$, $R^2$, $R^4$, and $R^5$ are as defined above;
(D) esterifying the compound of Formula V by reaction with methanesulfonyl chloride or toluenesulfonyl chloride to provide a reactive ester of Formula VI

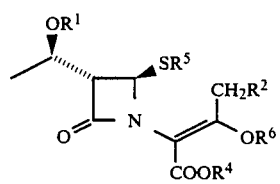

wherein $R^6$ is methanesulfonyl, or p-toluenesulfonyl, and
$R^1$, $R^2$, $R^4$, and $R^5$, are as defined above; and
(E) reacting the reactive ester of Formula VI with a thiol of the formula $R^3SH$ in the presence of a tertiary amine to provide thiol enol ester sulfide of Formula VIc,

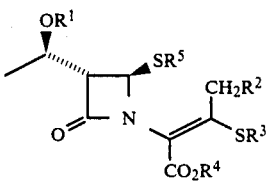

converting the $R^5S$-substituent of VIc to a better leaving group by oxidation to the sulfoxide or alkylation to a sulfonium group and thereafter cyclizing by intramolecular carbanionic displacement of the converted $R^5S$-substituent to provide the compound of formula I.

6. The process of claim 5, wherein the tertiary amine is diisopropylethylamine, and $R^3SH$ is methanethiol or thiophenol.

7. The process of claims 1 or 5, wherein $R^1$ is t-butyldimethylsilyl.

8. The process of claims 1 or 5, wherein $R^2$ is lower alkyl.

9. The process of claims 1 or 5, wherein $R^3$ is methyl, phenyl or 2-picolyl.

10. The process of claims 1 or 5, wherein $R^4$ is methyl, allyl or 2-chloroallyl.

11. The process of claims 1 or 5, wherein $R^5$ is methyl or phenyl.

* * * * *